United States Patent
Núñez Figueredo et al.

(10) Patent No.: US 11,098,039 B2
(45) Date of Patent: Aug. 24, 2021

(54) BENZODIAZEPINE PRODUCT WITH ACTIVITY ON THE CENTRAL NERVOUS AND VASCULAR SYSTEMS

(71) Applicants: UNIVERSIDAD DE LA HABANA, Havana (CU); CENTRO DE INVESTIGACIÓN Y DESARROLLO DE MEDICAMENTOS CIDEM, Havana (CU)

(72) Inventors: Yanier Núñez Figueredo, Havana (CU); Maylin Wong Guerra, Havana (CU); Luis Arturo Fonseca Fonseca, Havana (CU); Bárbara Beatriz Garrido Suárez, Havana (CU); Jeney Ramírez Sánchez, Havana (CU); Gilberto Lázaro Pardo Andreu, Havana (CU); Yamila Verdecia Reyes, Havana (CU); Estael Ochoa Rodríguez, Havana (CU); Pedro Gilberto Bárzaga Fernández, Havana (CU); Nicté González Alfonso, Havana (CU); René Delgado Hernández, Havana (CU); Alejandro Saúl Padrón Yaquis, Havana (CU)

(73) Assignees: UNIVERSIDAD DE LA HABANA, Havana (CU); CENTRO DE INVESTIGACIÓN Y DESARROLLO DE MEDICAMENTOS CIDEM, Havana (CU)

( * ) Notice: Subject to any disclaimer, the term of this patent is extended or adjusted under 35 U.S.C. 154(b) by 0 days.

(21) Appl. No.: 16/099,116

(22) PCT Filed: May 3, 2017

(86) PCT No.: PCT/CU2017/050002
§ 371 (c)(1),
(2) Date: May 23, 2019

(87) PCT Pub. No.: WO2017/190713
PCT Pub. Date: Nov. 9, 2017

(65) Prior Publication Data
US 2019/0270738 A1    Sep. 5, 2019

(30) Foreign Application Priority Data

May 4, 2016    (CU) .................................. 2016-0058

(51) Int. Cl.
C07D 471/04    (2006.01)
A61P 25/00    (2006.01)
A61P 25/16    (2006.01)
A61P 25/28    (2006.01)
A61K 31/551    (2006.01)

(52) U.S. Cl.
CPC ............ C07D 471/04 (2013.01); A61P 25/16 (2018.01); A61P 25/28 (2018.01)

(58) Field of Classification Search
CPC ........ C07D 471/04; A61P 25/00; A61P 25/16; A61P 25/28; A61K 31/551
See application file for complete search history.

(56) References Cited

U.S. PATENT DOCUMENTS

| | | | |
|---|---|---|---|
| 9,315,497 B2 | 4/2016 | Verdecia Reyes et al. | |
| 10,138,231 B2 | 11/2018 | Verdecia Reyes et al. | |
| 10,722,491 B2 | 7/2020 | Ochoa Rodriguez et al. | |
| 2019/0092769 A1 | 3/2019 | Verdecia Reyes et al. | |

FOREIGN PATENT DOCUMENTS

| | | |
|---|---|---|
| CU | 20090172 A6 | 10/2009 |
| WO | WO2009137462 A2 | 11/2009 |

OTHER PUBLICATIONS

International Search Report for corresponding PCT Application No. PCT/CU2017/050002, pp. 1-2 (dated Jul. 27, 2017).

*Primary Examiner* — Bruck Kifle
(74) *Attorney, Agent, or Firm* — Hoffmann & Baron, LLP

(57) ABSTRACT

Formula III compound, its products and pharmaceutical compositions containing them for the treatment of central nervous and vascular system diseases, particularly neurodegenerative disorders with cognitive deterioration, diseases associated with oxidative stress, diseases taking in mitochondrial dysfunction, Parkinson's disease and neuropathic pain, as well as the pathological processes associated with aging.

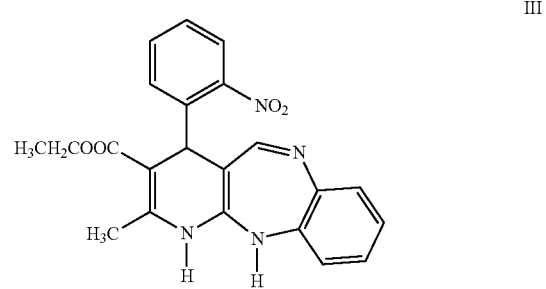

(JM-20)

17 Claims, 16 Drawing Sheets

Short-term Memory

A Acquisition

B Consolidation

Long-term Memory

A Acquisition

B Consolidation

BENZODIAZEPINE PRODUCT WITH ACTIVITY ON THE CENTRAL NERVOUS AND VASCULAR SYSTEMS

This application is the U.S. National Phase of, and Applicant claims priority from, International Patent Application Number PCT/CU2017/050002 filed 3 May 2017, which claims priority from CU 2016-0058 filed 4 May 2016, each of which is incorporated herein by reference.

INVENTION FIELD

This invention is related to the prevention and/or treatment of neurodegenerative diseases or diseases associated with cognitive deterioration, with unwanted oxidation or pathological processes associated with aging.

Neurodegeneration is a topic which is common to many diseases of the nervous system disorders such as dementias, Alzheimer's disease (AD), Parkinson's disease (PD) and neuropathic pain (NP). These diseases are devastating and it is expensive to manage them and the current treatments are inadequate. To the urgency of this problem we add the fact that incidence of these diseases related to aging is rapidly growing due to the demographic changes that are occurring.

The progressive aging of the world's population brings with it the unwanted consequence of increased neurodegenerative diseases and senile dementias. Worldwide, 46.8 million persons are estimated to be living with dementia. It is estimated that this number will grow to almost double every 20 years; to 74.7 million in 2030 and 131.5 million for 2050. Dementia also has an enormous economic impact. Today, the estimated world cost for dementia is 818 billion USD and it will become a trillion dollar disease by 2018, with a tremendous impact on the quality of life of both patients and their family members and caretakers (Alzheimer's Disease International. World Alzheimer Report 2015. London: Alzheimer's Disease International; 2015).

Of all these, AD is the most prevalent with approximately 35 million persons suffering from the disease and it is estimated that its incidence is significantly going to grow in the next three decades, keeping pace with the average age of the population (Reitz, C.; Brayne, C.; Mayeux, R. Epidemiology of Alzheimer's disease. Nat. Rev. Neurol., 2011, 7, 137-152) (Reitz, C.; Mayeux, R. Alzheimer's disease: Epidemiology, diagnostic criteria, risk factors and biomarkers. Biochem. Pharmacol., 2014, 88, 640-651).

AD is a neurodegenerative disorder of the brain leading to memory loss and the loss of cognitive functions progressing at a slow pace, often accompanied by behavior changes such as aggression and depression (Querfurth, H. W.; LaFerla, F. M. Alzheimer's disease. N. Engl. J. Med., 2010, 362, 329-344). In its last stage, patients are bedridden, incontinent and dependent on care, something which is very expensive for the families. On an average, death occurs 9 years after diagnosis (Citron M. (2004). Strategies for disease modification in Alzheimer's disease. Nat Rev Neurosci. 5(9): 677-85). The great numbers of persons suffering from this disease, requiring round the clock care and other services will severely affect medical, monetary and human resources (Suh Y. H. and Checler F. (2002). Amyloid precursor protein, presenilins, and alpha-15 synuclein: molecular pathogenesis and pharmacological applications in Alzheimer's disease. Pharmacol Rev. 54(3): 469-525). Amyloid precursor protein, presenilins, and alpha-15 synuclein: molecular pathogenesis and pharmacological applications in Alzheimer's disease. Pharmacol Rev. 54(3): 469-525). Therefore this is a growing medical concern. AD is a protoypical cortical dementia characterized by memory loss along with dysphagia (language disorder with deteriorated speech and conversation comprehension), dyspraxia (disability in coordination and execution of certain movements and intentional gestures in the absence of motor deterioration) and agnosia (the ability to recognize objects, persons, sounds, shapes and or odors) attributed to the involvement of cortical association areas (Crook R. et al. (1998). A variant of Alzheimer's disease with spastic paraparesis and unusual plaques due to deletion of exon 9 of presenilin 1. Nat Med. 4(4): 452-5) (Houlden H., Baker M., et al. (2000). Variant Alzheimer's disease with spastic 5 paraparesis and cotton wool plaques is caused by PS-1 mutations that lead to exceptionally high amyloid-beta concentrations. Ann Neurol. 48(5): 806-8) (Kwok J. B., Taddei K., et al. (1997). Two novel presenilin-1 mutations in early-onset Alzheimer's disease pedigrees and preliminary evidence for association of presenilin-1 mutations with a novel phenotype. Neuroreport. 8(6): 1537-42) (Verkkoniemi A., Kalimo H., et al. (2001). Variant Alzheimer disease with spastic paraparesis: neuropathological phenotype. J Neuropathol Exp Neurol. 60(5): 483-92).

Although the disease is multifactorial and heterogeneous, it has certain common characteristics such as massive losses of cholinergic neurons, deposition of neurofibrillary tangles and beta-amyloid aggregates (Huang, Y.; Mucke, L. Alzheimer Mechanisms and Therapeutic Strategies. Cell, 2012, 148, 1204-1222).

The chemical pathology of AD shows many similarities to Parkinson's disease (PD): oxidative stress, reduced activity of the mitochondrial complex I, increased lipid peroxidation. These similarities also include the progressive nature of the disease, the proliferation of reactive microglia around dying neurons, oxidative stress and inflammatory processes.

Despite great investments made by the pharmaceutical industry, there are few, in fact no efficacious treatments for AD.

Today different strategies are being followed to obtain new drugs to treat the disease, given that we have seen that currently approved drugs provide few benefits for patients. These drugs temporarily delay (for one year in the best of cases) some of the symptoms of the disease but they do not prevent its evolution.

Even though initially AD was associated only with a cholinergic deficiency, it has been shown that other neurotransmitters such as dopamine, noradrenalin, serotonin and glutamate are reduced or unregulated in AD. Currently the neurotransmitters most studied in AD pathogenesis are cholinergic and glutamatergic (Palmer, A M; Gershon, S. Is the neuronal basis of Alzheimer's disease cholinergic or glutamatergic? FASEB J 1990, 4, 2745-52).

Current AD therapeutic options are based on the inhibition of acetylcholinesterase with drugs such as donepezil, galantamine or rivastigmine or on the capacity of memantine to antagonize the glutamate receptor, NMDA (N-methyl-D-aspartate. Due to the low success rate of these drugs, new lines of research have opened up. (Bartus, R T, Dean, R L 3rd; Beer, B; Lippa, A S The cholinergic hypothesis of geriatric memory dysfunction. Science 1982, 217, 408-14) (Terry, A. V. Jr.; Buccafusco, J. J. The cholinergic hypothesis of age and Alzheimer's disease-related cognitive deficits: recent challenges and their implications for novel drug development. J. Pharmacol. Exp. Ther., 2003, 306, 821-827) (van Marum, R. J. Current and future therapy in Alzheimer's disease. Fundam. Clin. Pharmacol., 2008, 22, 265-274)

In accordance with the cholinergic hypothesis of AD, the loss of cholinergic functions in the central nervous system (CNS) contributes significantly to cognitive dysfunction associated with AD (Bartus, R.; Dean, R.; Beer, B.; Lippa, A. The cholinergic hypothesis of geriatric memory dysfunction. *Science,* 1982, 217, 408-414). Also, even though the relationship between cholinergic depletion, amyloidogenesis and Tau phosphorylation is complex, it seems that reduction of the cholinergic may increase B amyloid production and it may induce the phosphorylation of the Tau protein. On the other hand, AD's glutamatergic hypothesis establishes that the excitotoxic mechanisms related with glutamate involve the NMDA receptor leading to degeneration and cell death (Bleich S, Romer K, Wiltfang J, Komhuber J. Glutamate and the glutamate receptor system: a target for drug action. Int J Geriatr Psychiatry 2003, 18, S33-40). Synaptic stimulation through NMDA receptors is important for functions in learning and memory, but an excess of glutamate may cause excitotoxicity and neurodegeneration (Michaels R L, Rothman S M Glutamate neurotoxicity in vitro: antagonist pharmacology and intracellular calcium concentrations. J Neurosci 1990 10, 283-92).

In this scenario treatment strategies should exercise impediments for both systems by a combination of an AChe enzyme inhibitor capable of improving cholinergic tone with an NMDA receptor antagonist capable of contrasting with the glutamate induced neurodegeneration. Nevertheless, this combination of therapies presents some disadvantages. Besides confronting the administration of separate drugs, something creating an additional problem for elderly patients suffering from AD and for the persons looking after them, the different pharmacokinetics of the respective drugs may impact in different pharmacodynamics. In practice, clinics would confront the administration of a combined therapy of two different ADME (Administration Distribution Metabolism Excretion) curves.

An alternative and innovative approach to the combination of two medications is for drugs which can act on multiple pharmacological targets, the so-called multi-target drugs (MTD).

The strategy of acting on two or more proteins at the same time with a simple compound may provide superior therapeutic effects (Cavalli A, Bolognesi M L, Minarini A, Rosini M, Tumiatti V, Recanatini M, Melchiorre C. Multi-target-directed ligands to combat neurodegenerative diseases J Med Chem 2008, 51, 347-72) (Zimmerman G R, Lehar J, Keith C T. Multi-target therapeutics; when the whole is greater than the sum of the parts. Drug Discov Today 2007, 12, 34-42) (Morphy R, Ranlovic, Z. Fragments, network biology and designing multiple ligands. Drug Discov Today 2007, 12, 156-60). This may be explained by the number of potential benefits provided by the use of the MTDs over cocktails or multi-component medications. The advantages of MTDs over the cocktails may be summed up as: 1) reducing the uncertainty in clinical development, given that predicting the pharmacokinetics of a simple compound is much easier than that of a cocktail, overcoming the problem of different bio-availabilities, pharmacokinetics and metabolisms; 2) pharmacodynamics safety; 3) increased efficacy due to the synergic effect of inhibiting multiple therapeutic targets, and 4) increased safety upon decreasing the secondary effects of consuming drug cocktails (reduced risks due to drug-drug interactions); this particularly relevant for drug metabolism where the competition of different drugs for the same metabolic enzyme affect their toxicity.

Another important advantage is a simplified therapeutic regime with improved possibilities for compliance and this is especially important for elderly Alzheimer patients and their caretakers (Small, G, Dubois B A review of compliance to treatment in Alzheimer's disease: potential benefits of a transdermal patch. Curr Med Res Opin 2007, 23, 2705-13). In regards to this, an important aspect is that Alzheimer patients are susceptible to a wide range of medical conditions (comorbidity) that include hypertension, vascular diseases and diabetes which may often be associated. Therefore problems associated with multi-pharmaceutical use in the geriatric population have been recognized as critical in recent years. These problems primarily consist of drug interactions, something which occurs more frequently in this population due to the coexistence of chronic illnesses and organ failures. One cannot assume that two drugs which by themselves are safe would also be safe when combined, particularly in the geriatric population. Also the number of drugs administered at the same time should be reduced as much as possible since advanced age is an unpredictable risk factor for any drug treatment (Turnheim, K. When drug therapy gets old: pharmacokinetics and pharmacodynamics in the elderly. Exp. Geront. 2006, 38, 843-853). Since MTDs are strongly favored over combination therapies in regards to the complexity of interactions among multi-functional drugs, comorbidities, altered pharmacodynamics sensibilities and changes in pharmacokinetics in the elderly. Clinical use of MTDs can also simplify the therapeutic regime (Youdim, M. B., and Buccafusco, J J (2005) CNS Targets for multi-functional drugs in the treatment of Alzheimer's and Parkinson's diseases J. Neural Transm 112, 519-537). Compliance with prescribed medication regimes is essential for effective treatment. Noncompliance represents a general problem but this is a challenge for Alzheimer patients and their caretakers (Small, G, Dubois B A review of compliance to treatment in Alzheimer's disease: potential benefits of a transdermal patch. Curr Med Res Opin 2007, 23, 2705-13). Consequently, a simplified treatment regime with drugs acting on multiple targets could increase adherence to the treatment. All the prior advantages mentioned are not available for drug cocktails.

The ligand 1 strategy for multiple targets is an innovative approach for developing new candidates for the treatment of complex neurological diseases, especially with a view to the fact that the basic processes involved in neurodegenerative diseases are by nature multi-factorial (Cavalli A, Bolognesi M L, Minarini A, Rosini M, Tumiatti V, Recanatini M, Melchiorre C. Multi-target-directed ligands to combat neurodegenerative diseases J Med Chem 2008, 51, 347-72). Such a strategy is based on the concept that one single compound can act on multiple targets cooperating in the neurodegenerative process implicit in Alzheimer's and in other neurodegenerative diseases and which therefore would foresee the unwanted compensation between interacting pathogenic routes. But MTDs can represent an alternative practice to the use of drug combinations. Since the majority of neurodegenerative mechanisms are shared by many neuronal diseases these MTDs can also be used as medication for other diseases.

The global burden of ischemic stroke is nearly 4 times greater than the hemorrhagic stroke. Current proof suggests that 25 to 30% of ischemic stroke survivors develop immediate or delayed vascular cognitive deterioration or vascular dementia. Dementia after stroke injury may include all types of cognitive disorders. Since risk of death after strokes has diminished, the number of stroke survivors having cerebral affectation and cognitive deterioration has increased (R. N. Kalaria, et al., Stroke injury, cognitive impairment and vascular dementia, Biochim. Biophys. Acta (2016), http://dx.doi.org/10.1016/j.bbadis.2016.01.015).

Post-stroke dementia is considered to be a clinical entity defining all types of dementia occurring after stroke injury, apart from whether it includes vascular, neurodegenerative or a combination of the two processes. That entails complex etiology with variable combinations of diseases of the large and small vessels as well as neurodegenerative pathologies (R. N. Kalaria, et al., Stroke injury, cognitive impairment and vascular dementia, Biochim. Biophys. Acta (2016), http://dx.doi.org/10.1016/j.bbadis.2016.01.015).

From the knowledge we have about the cascade of ischemic injuries, we know that it consists of a series of complex events that are highly heterogenic (R. Brouns, P. P. De Deyn, The complexity of neurobiological processes in acute ischemic stroke, Clin. Neurol. Neurosurg. 111 (2009) 483-495) evolve from minutes to days and weeks after the initial hypoperfusion event. Principal events include energy failures due to the interrupted blood flow, excitotoxicity, calcium overloading, oxidative stress, blood brain barrier dysfunction, microvascular damage, hemostatic activation, injuries related to inflammatory and immune responses and cell death on the level of neuronal, glia and endothelial cells. Microvascular injuries and the disruption of the hemato-cephalic barrier which could occur days later leads to vasogenic edema and may also cause hemorrhages. At the same time the tissues may undergo a complex range of repair and remodeling responses which include angiogenesis to limit the damage and to improve the consequences. These events are truncated in aging brains so that the parenchyma is irreversibly injured thereby contributing to cognitive dysfunction (R. N. Kalaria, et al., Stroke injury, cognitive impairment and vascular dementia, Biochim. Biophys. Acta (2016), http://dx.doi.org/10.1016/j.bbadis.2016.01.015).

Experimental studies suggest that cellular death after ischemic impairment is highly attributable to necrosis. Nevertheless recent developments indicate that neuronal death occurs significantly by apoptosis as well as by hybrid mechanisms (R. N. Kalaria, et al., Stroke injury, cognitive impairment and vascular dementia, Biochim. Biophys. Acta (2016), Neuroinflammation and immunodepression are also associated with stroke, aging and infection. This probably has a damaging effect on cognitive function after strokes (B. W. McColl, S. M. Allan, N.J. Rothwell, Systemic inflammation and stroke: aetiology, pathology and targets for therapy, Biochem. Soc. Trans. 35 (2007) 1163-1165) (C. Meisel, A. Meisel, Suppressing immunosuppression after stroke, N. Engl. J. Med. 365 (2011) 2134-2136) (W. Swardfager, D. A. Winer, N. Herrmann, S. Winer, K. L. Lanctot, Interleukin-17 in post-stroke neurodegeneration, Neurosci. Biobehav. Rev. 37 (2013) 436-447).

Parkinson's disease (PD) is a neurodegenerative disease with symptoms of motor dysfunction, slow movements, rigidity, tremors in repose and alterations to equilibrium. As the disease advances, many patients develop non-motor symptoms including anxiety, depression, constipation and dementia. These characteristics are attributed to the great reduction in dopamine striatal content and a loss of dopaminergic neurons in the compact *nigra pars* matter (Gauthier, 1982).

The clinical signs of PD appear after dopaminergic neuronal death exceeds a threshold of 70 to 80% and a loss of striate nerve endings exceeding 50 to 60% (Agid, 1991).

Research on the development mechanisms of PD have indicated that dopaminergic neuron loss in the compact *nigra pars* matter is related to deficiency in the mitochondrial complex I (Jenner 1998).

Even though there are drugs which alleviate Parkinson symptoms, the chronic use of these drugs is not effective in preventing PD's progression and it has been associated with debilitating secondary effects. Therefore it is of great interest to develop neuroprotector therapies that delay or even stop the degenerative progression.

Unfortunately the development of neuroprotector therapies has been hampered by limited knowledge of the pathogenesis of degenerative neurological diseases such as PD. The etiology and pathogenesis responsible for the neural deterioration of Parkinson's is still unknown. Some lines of proof support the theory of the activation of microglia and inflammatory processes are involved in the cascade of events leading to progressive neuron degeneration (Kreutzgber, G W, 1996 Trends Neurosci, 19:312-318). Activated microglia is present in the vicinity of the neurons in degeneration in the nigra matter of Parkinson's patients (McGeer, P L et al, 1988, Neurology, 38:1285-1291).

The course of classic PD treatment is the administration of dopamine agonists such as levodopa (L-DOPA) and carbidopa. Other drug agents with the express aim of either replacing dopamine or inhibiting its degradation, such as the inhibitors of catecol-O-methyltransferase and amantadine are commonly prescribed (N. L. Diaz, C. H. Waters, Expert Rev Neurother 9, 1781 (Dec. 1, 2009).

While such drug agents typically improve patient symptoms, they are not always effective and/or tolerated over time, with dyskinesia being a secondary effect (A. H. Schapira et al., European Journal of Neurology 16, 1090 (2009)). Another complication is the fact that daily treatments may be burdensome and lessen patient adherence to medication. Therefore today emphasis is being put on new systems of drug liberation which are capable of providing continuous infusions of dopamine agonists by placing minipumps (e.g. intrajejunal, subcutaneous) and for liberation through the skin via dermal patches (A. H. Schapira et al., European Journal of Neurology 16, 1090 (2009)). Even with the evolution of such drugs and their liberation systems, some Parkinson's patients nevertheless still do not receive sufficient relief (N. L. Diaz, C. H. Waters, Expert Rev Neurother 9, 1781 (Dec. 1, 2009).

Experimental models of mitochondrial diseases typically involve the inhibition of enzymes involved in the electron transportation chain (1). It has also been reported that many of the neurodegenerative diseases are associated with mitochondrial dysfunction (2-5). Defects in I, II and IV complexes in the mitochondrial respiratory chain have been detected in Alzheimer's, Parkinson's, Huntington's and Lou Gehrig's diseases (6-9).

Some lines of proof imply that Parkinson's is a disease that involves free radicals and a mitochondrial dysfunction leading to the failure of energy production (10-11). Increased oxidative damage, dopamine depletion, the nitration of proteins, accumulation of iron, addition of proteins and apoptosis are characteristics of Parkinson's disease (12-14).

Multiple epidemiological studies show that chronic pain is highly prevalent with serious impact on the health of individuals, health and societal services (Torrance N, Smith B H. Bennett M I, Lee A J. The epidemiology of chronic pain of predominantly neuropathic origin. Results from a general population survey. J Pain 2006; 7:281-289) (Treede R D, Jensen T S, Campbell J N, Cruccu G, Dostrovsky J O, Griffin µW, Hansson P, Hughes R, Nurmikko T, Serra J. Redefinition of neuropathic pain and a grading system for clinical use: consensus statement on clinical and research diagnostic criteria. Neurology 2008; 70:1630-1635). It has particularly been estimated that chronic pain with neuropathic content affects approximately 7 to 8% of the general population and the therapies available for its treatment are as yet unsatisfactory (Torrance N, Smith B H. Bennett M I, Lee A J. The epidemiology of chronic pain of predominantly neuropathic origin. Results from a general population survey. J Pain 2006; 7:281-289) (van Hecke O, Austin S K, Khan R A, Smith B H, Torrance N. Neuropathic pain in the general population: a systematic review of epidemiological studies. Pain 2014; 155:654-62) (Bennett M I, Rayment C, Hjermstad M, Aass N, Caraceni A, Kaasa S. Prevalence and aetiology of neuropathic pain in cancer patients: A systematic review. Pain 2012; 153:359-365). NP is considered a symptom of neurodegeneration, subsequently it is logical to consider neuroprotection as a strategy to prevent its start, control its progression and even to revert neural injuries leading to the establishment of these chronic pain symptoms (Bordet T and Pruss R M. Targeting neuroprotection as an alternative approach to preventing and treating neuropathic pain. Neurotherapeutics 2009; 6:648-662). Neuroprotection includes methods that maintain neuron survival or their function in the context of pathological stress (traumatic, toxic, ischemic or metabolic events). Hence today the treatment of most periphery and central NP neuropathies (painful diabetic neuropathy, distal polyneuropathy, sensorial distal by HIV and antiretroviral therapies, peripheral neuropathies induced by chemotherapy, post-herpetic neuralgia, MS pain and post-stroke pain, etc.) is being directed towards that prospect (Bordet T and Pruss R M. Targeting neuroprotection as an alternative approach to preventing and treating neuropathic pain. Neurotherapeutics 2009; 6:648-662) (Flatters S J L, Bennett G J. Studies of peripheral sensory nerves in paclitaxel-induced painful peripheral neuropathy: Evidence for mitochondrial dysfunction. Pain 2006; 122: 245-257) (Jaggi A S, Singh N. Mechanisms in cancer-chemotherapeutic drugs-induced peripheral neuropathy. Toxicology 2012; 291:1-9). There is a particular focus on glutamatergic dysfunction, nitro-oxidative stress, mitochondrial dysfunction, apoptosis, trophic factors, neuroinflammation and changes in the uninjured fibers induced by neurodegeneration (Bordet T and Pruss R M. Targeting neuroprotection as an alternative approach to preventing and treating neuropathic pain. Neurotherapeutics 2009; 6:648-662) (DeLeo J A, Sorkin L S, Watkins L R, editors. Immune and glial regulation of pain. Seattle: IASP Press; 2007) (Park E S, Gao X, Chung J M, Chung K. Levels of mitochondrial reactive oxygen species increase in rat neuropathic spinal dorsal horn neurons. Neuroscience Letters 2006; 391:108-111). A biologist approximation has been suggested in the development of novel therapies for pain based on the participation of the electron transportation chain in neuropathies dependent on ATP (Joseph E K, Levine J D. Mitochondrial electron transport in models of neuropathic and inflammatory pain. Pain 2006; 121:105-114) (Joseph E K, Levine J D. Multiple P KCc-dependent mechanisms mediating mechanical hyperalgesia. Pain 2010; 150:17-21). Mitochondrial dependence of the nerve growth factor (NGF) in the induction of mechanical hyperalgesia has also been reported (Chu C, Levine E, Gear R W, Bogen O, Levine J D. Mitochondrial dependence of nerve growth factor-induced mechanical hyperalgesia. Pain 2011; 152:1832-1837).

In accordance with these ideas, multiple immune mediators involved in the process of Wallerian degeneration (WD) which occurs when the continuity of the nerve fiber is interrupted have been proposed as new targets for drug treatment of NP (Debový P. Wallerian degeneration and peripheral nerve conditions for both axonal regeneration and neuropathic pain induction. Annals of Anatomy 2011; 193: 267-275) (Lingor P, Koch J C, Tönges L, Bähr M. Axonal degeneration as a therapeutic target in the CNS. Cell Tissue Res 2012; 349:289-311). The role played by neuroimmune activation, microglia-neuron signalization and oxidative stress has also been recognized in the reinforcing of transmission after nerve injuries (Berger J V, Knaepen L, Janssen S P M, Jaken R J P, Marcus M A E, Joosten E A J, Deumens R. Cellular and molecular insights into neuropathy-induced pain hypersensitivity for mechanism-based treatment approaches. Brain Research Reviews 2011; 67: 282-310) (De Leo J. A, Tawfik V L, La Croix-Fralish M L. The tetrapartite synapse: Path to CNS sensitization and chronic pain. Pain 2006; 122:17-21) (Austin P J, Moalem-Taylor G. The neuro-immune balance in neuropathic pain: Involvement of inflammatory immune cells, immune-like glial cells and cytokines Journal of Neuroimmunology 2010; 229:26-50) (Salvemini D, Little J W, Doyle T, Neumann W L. Roles of reactive oxygen and nitrogen species in pain. Free Radical Biology & Medicine 2011; 51:951-966). Consequently, innovative strategies directed towards neuroprotection and particularly neuroinflammation for NP treatment are today found in the research-development stage (Bordet T and Pruss R M. Targeting neuroprotection as an alternative approach to preventing and treating neuropathic pain. Neurotherapeutics 2009; 6:648-662) (Stavniichuk R, Drel V R, Shevalye H, Maksimchyk Y, Kuchmerovska T M, Nadler J L, Obrosova I G. Baicalein alleviates diabetic peripheral neuropathy through inhibition of oxidative-nitrosative stress and p38 MAPK activation. Experimental Neurology 2011; 203:106-113).

Aging and neurological and psychiatric disorders cause injury to and death of nerve cells. Among the frequent and relevant nervous system lesions we include, among others, neuron degeneration, ischemia, inflammation, immune responses, trauma and cancer. As a result of these, nerve cells may die in minutes or hours or they may survive the initial lesion in an injured state activating neurodegeneration and finally also ending in cell death.

Neurodegeneration in Parkinson's, Alzheimer's and other neurodegenerative diseases seem to be multifactorial so that a complex range of toxic reactions including inflammation, glutamatergic neurotoxicity, increased iron and nitric oxide, depletion of endogen antioxidants, reduced expression of trophic factors, dysfunction of the ubiquitin proteasome system and expression of proapoptotic proteins lead to the death of neurons.

Given the importance of the nervous system in making possible basic motor skills and sensibility, there is interest in finding therapeutic weapons to protect the nervous system.

Neuroprotection is directed towards conservation, recovery, curing or regenerating the nervous system, its cells, structure and function (Vajda et al 2002, J Clin Neurosci 9:4-8). One aim of neuroprotection is to prevent or minimize the effects of an original lesion in the nervous system, or to prevent or minimize the consequences of endogenous or exogenous harmful processes that cause injury in the axons, neurons, synapsis and dendrites.

Neuroprotection is the mechanism and strategy used to protect against neuron injury or CNS degeneration as the result of chronic neurodegenerative diseases (Alzheimer, Parkinson). The aim of neuroprotection is to limit the dysfunction/death after injury to the CNS and to attempt to maintain the greatest possible integrity for cellular interactions in the brain resulting in undisturbed neural function.

The concept of neuroprotection was applied to chronic brain diseases as well as to acute neurological conditions, given that some of the basic mechanisms injuring the CNS are similar to these conditions. Neurodegenerative disorders include AD, PD, Huntington's disease and Lateral Amyotrophic Sclerosis. Neuroprotection has been considered as the drug action mechanism used for the treatment of these conditions.

There is a broad range of neuroprotector products available or being researched and some products may potentially be used for more than one disease given that many of the mechanisms for injuries to neural tissues are similar. Products with neuroprotector effects are grouped into the following categories: kidnappers of free radicals, antiexcitotoxic agents, inhibitors of apoptosis (programmed cell death), anti-inflammatory agents, neurotrophic factors, chelating metal ions, ion channel modulators and genic therapy.

It has been demonstrated that oxygen free radicals are associated with the denaturalization of proteins, inactivation of enzymes and DNA damage resulting in lipid peroxidation of cell membranes and finally cell death in neurodegenerative diseases.

Studies carried out on both animal and human models show that the loss of equilibrium among oxidant species generated by the cerebral metabolism and antioxidant protector mechanisms produce the so-called oxidative stress when said defense systems decrease their efficacy and are breached, This oxidative stress increases with age and is found among the prime causes of AD pathogenesis (*Neurobiol. Aging* 2007, 28, 1009-1014) possibly associated with neuron mitochondrial dysfunctions. We also know that products with antioxidant properties are capable of preventing apoptosis induced by the amyloid peptide as well as changes to $Ca^2$ homeostasis in cultures of cortical neurons (*Life Sci.* 2000, 66, 1879-1892). 66, 1879-1892). Consequently, there is a great need for acetylcholinesterase (AChE) or butirilcholinesterase (BuChE) inhibitors, and with neuroprotector capacity for toxic insults such as oxygenated free radicals, said compounds would have great medical importance in the treatment of neurodegenerative diseases such as AD, PD or Huntington's.

Generally speaking, treatment strategies are frequently based on the modulation of a single factor of the proposed lesion. Although we can observe that said treatments are beneficial in very limited animal; models, it is less likely that they would show themselves to be efficacious in more complex human disorders involving more variable degrees of lesion severity in a genetically diverse population (Faden and Stoica 2007; Arch Neurol 64:794-800). To a great extent, given the presumed mechanisms of neuron death such as oxidative stress, mitocondrial dysfunction, added proteins, apoptosis and inflammation (Youdim, M. B., and Buccafusco, J J (2005) CNS Targets for multi-functional drugs in the treatment of Alzheimer's and Parkinson's diseases J. Neural Transm 112, 519-537), they are as complex as they are varied, we would want single compounds that have multi-purpose effects on the multiple mechanisms of lesions.

BRIEF DESCRIPTION OF THE INVENTION

The compound (3-etoxicarbonil-2-methyl-4-(2-nitrofeenil)-4,11-dihydro-1H-pirido[2,3-b][1,5] benzodiacepine) (JM-20) which is described in the document for Cuban Patent CU23879 by its chemical structure may have effects on cardiovascular, cerebrovascular and other diseases associated with the central nervous system.

Surprisingly researchers have discovered that compound JM-20 has marked therapeutic effects on the CNS preferably for the treatment of diseases such as different types of dementia, Parkinson's and pain.

Therefore the essence of this invention is based on the use of JM-20 and its chemical products to be used preferentially in the treatment of diseases such as the different types of dementia, Parkinson's and pain.

JM-20 is a product of benzodiacepine and it has been widely reported that benzodiacepines induce dementias (Huber-Geismann, F, 1994) (Rosenberg, P. B. 2015). (Shash, D., T. Kurth, et al. 2015) (Zhong, G., Y. Wang, et al. 2015)), but unexpectedly JM-20 improves different types of dementias.

In spite of the fact that the potential usefulness f JM-20 has been reported in literature, its potential as a therapeutic drug in neurodegenerative diseases such as dementias, Parkinson's and neuropathic pain has not been established.

As an additional aspect to this invention, the general formula III compound (JM-20), its salts, hydrates, crystalline forms, enantiomers, isomers, metabolites, physiologically tested prodrugs may be administered mixed with at least one vehicle agent, diluent and/or carrier, chemically inert, nontoxic, hereafter recognized as excipients included in the drug compositions being proposed.

BRIEF DESCRIPTION OF THE FIGURES

FIGS. 24 C & D. Effects of JM-20 on the peritoneal inflammatory response induced by carragenin (500 µg/cavity) C. Migration of leukocytes towards the peritoneal cavity and D. vascular permeability. Effect of JM-20 (40 mg/Kg, 10 mL/Kg, p.o.) or vehicle (CMC, 0.05%) on peritoneal inflammatory response induced by carragenin (500 pg/cavity). C. Migration of leukocytes to the peritoneal cavity and D. vascular permeability (pg/mL) were determined 4 h post-CA. Data is presented as mean±SEM of the neutrophil count/cavity, n=6 per group, *p<0.05, ***p.<0.01 represent significant differences relative to control group treated with vehicle ###p<0.001 represent significant differences related to control with intraperitoneal saline (one way ANOVA followed by Bonferronni's a posteriori).

FIG. 24 E: Effects of JM-20 on concentrations of the tumor necrosis factor (TNFα) in the peritoneal fluid 4 hours after the carragenin injection. Effect of JM-20 (20 mg/Kg, 10 mL/Kg, p.o.) or vehicle (CMC, 0.05%) on tumor necrosis factor (TNFα) concentrations in the peritoneal fluid after 4 h of carragenin injection. Data is presented as mean±SEM, n=6 per group *p<0.05 represent significant differences with respect to the control group treated with vehicle ####p<0.05 represent significant differences relative to control with intraperitoneal saline (one way ANOVA followed by Bonferronni's a posteriori).

DETAILED DESCRIPTION OF THE INVENTION

Figure 1:
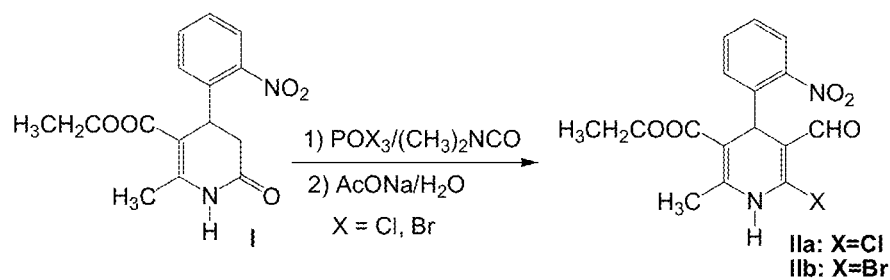
FIG. 1. Synthesis of compounds IIa and IIb.

The drug compositions provide for any liquid, solid or semi-solid composition, they can be administered orally, bucopharingeal, sublingual, parental, for example: intramuscular, intravenous, intradermal or subcutaneous, topical, transdermal, tracheal, bronchial, nasal, pulmonary, rectal or other suitable ways of administration.

The described drug compositions will include suitable excipients for each formula. Formulations are prepared conventionally using methods collected in the state of the art. Excipients are selected for their drug form of choice according to the way they will be administered.

The general formula III compound (JM-20), its salts, hydrates, crystalline forms, enantiomers, isomers, metabolites, prodrugs for its administration to humans may be contained in pharmaceutically acceptable forms of doses among which are but not limited to these forms of presentation: tablets (including sublinguals, coated and chewables), hard and soft capsules (including microcapsules, nanoparticles and pellets), solutions (oral drops, syrups), parenteral solutions, transdermal patches, implants and other retard systems, unguents (creams and gels), nasal sprays, mucous-adhesives, suppositories, suspensions, powders to be reconstituted or to be added to food, among other forms of doses included in this invention.

Using known technological processes in the state of the technique, JM-20, its salts, hydrates, crystalline forms, enantiomers, isomers, metabolites, prodrugs they may be formulated in dose forms adapted to their administration, mixing them with excipients such as auxiliary liquid, solid or semi-solid substances, composed of organic and inorganic natures, of natural or synthetic origins. Some of those included are: filled solids, diluents, agglutinants, solvents, emulsions, lubricants, disintegrations, sliding, flavoring, coloring, pigmented, polymers, sweeteners, plasticization, absorption potential, penetration potential, surfactants, co-surfactants, specialized oils and/or buffer systems that give the active compounds or their physiologically acceptable salts physical, chemical and/or biological stability. Some excipients used in the formulation of the forms of doses containing the general formula III compound or its products, without being limited to the use of other auxiliary substances, are: starches, lactose, cellulose and its products, sucrose, sorbitol, manitol and other sugars, talcum, colloidal silicon dioxide, carbonates, magnesium oxides, calcium phosphates, titanium dioxide, polyvinyl pyrolidone, povidone, gelatin, lacto-proteins, citrates, tartrates, alginates, dextran, ethyl cellulose, cyclodextrines, silicone elastomers, polysorbates, amylopectin, parabens, animal and vegetable oils, propylene glycol, sterilized water, mono or poly hydroxylic alcohols such as glycerol, magnesium stearate, calcium stearate, sodium stearyl fumarate, sodium lauryl sulfate, glycerin and polyethylene glycol waxes among others.

Solid oral forms of doses such as tablets, micro-granules, nanoparticles, pellets, powders to be reconstituted or capsules containing the general formula III or its salts, enantiomer forms and oxidation-reduction products according to this invention may be used for immediate or modified liberation.

A drug form of choice, according to this invention, are tablets containing as their active pharmaceutical ingredient the general formula III or its salts, hydrates, crystalline forms, enantiomers, isomers, metabolites, prodrugs prepare a mixture with micro-crystalline cellulose, cornstarch, crospovidone, adding dissolved polyvinyl pyrrolidone and sodium lauryl sulfate to form a granulate which is dried in a full process in a fluidized bed and mixed with magnesium stearate and talcum, subsequently tablets are made using a system of rotating punches for its manufacture, finally the tablets are coated with a hydroxyl propyl cellulose, polyethylene glycol 4000, titanium dioxide and coloring suspension.

By coating tablets we achieve an elegant finished look and we avoid the unpleasant taste; this is achieved with a flavor-masking agent such as co-polymer of methyl acrylic acid, ethyl celluloses, methyl hydroxyl propyl cellulose or other polymers. Tablets may be obtained both by the wet granulation method explained above and by the direct compression method using excipients for direct compression and decreasing steps in the phase of obtaining tablets, provided that one is working with low doses.

Tablets may be modified liberation and they may contain the general formula III or its products in micro-granules, nanoparticles or matrix systems, using excipients such as: polyethylene oxide, hydroxyl propyl cellulose 2910, magnesium stearate, sodium chloride, red ferrous oxide, cellulose acetate, polyethylene glycol 3350 and opadry.

According to this invention, drug compositions may contain pharmaceutically acceptable polymers, permeable, biodegradable and insoluble in water, to control its liberation profile thereby obtaining modified liberation (immediate, delayed or controlled) forms of doses. These polymers may be used to coat the tablets, micro-granules, capsules in obtaining nanoparticles, as liberation matrixes in pellets, tablets, granules or mixes with other excipients included in any other form of dose mentioned in this invention.

For oral administration, other suitable pharmaceutical compositions are hard capsules, soft capsules and pharmaceutical powders, the general formula III compound or its salts, enantiomer forms and products of its physiologically acceptable oxidation-reduction may be dosed in the form of hard gelatin or cellulose capsules for example, containing inside a mix of the active pharmaceutical ingredient with commonly used excipients in solid forms such as those described for tablets; said mix may be obtained by the dry route, wet granulation, extrusion, pelletization, micro-capsulation or micro-tab doses. For doses in soft gelatin capsules we use conventional manufacturing methods and they may be prepared mixing the general formula III compound or its salts, hydrates, crystalline forms, enantiomers, isomers, metabolites, prodrugs with vegetable oils, grease or other similar vehicles suitable for their formation.

In the case of pharmaceutical powders, these may be manufactured by simple mixtures of the general formula III (JM-20) compound or its salts, enantiomer forms and products of its physiologically acceptable prodrugs with fillers, suspension agents, sweeteners, flavors and preservatives. Although this invention also used the atomization-drying method at entry temperatures of between 100° C.-150° C. and exit temperatures of between 50° C.-90° C. in the elaboration of powders, using excipients such as dextran, polyethylene glycol 4000 and sodium lauryl sulfate, among others, to improve the solubility of the active pharmaceutical ingredient for its proper incorporation into the organism in solutions, or adding it to food such as juices.

For rectal administration, the general formula III compound (JM-20) or its salts, hydrates, crystalline forms, enantiomers, isomers, metabolites, physiologically acceptable prodrugs may be dosed as suppositories, foams or rectal microenema solutions which may contain a mixture of active compounds with a base of neutral solid fat (Witespol 45) or some other similar vehicle suitable for its formulation; sorbitan monooleate, polysorbate 20, emulsifier wax, anhydrate colloidal silicone, sodium meta bisulfite, disodium edatate, methyl parahydroxylbenzoate, sodium phosphates, macrogol 300, glycerin, water, propane, isobutene and n-butane.

For liquid oral administration the general formula III compound (JM-20) or its salts, hydrates, crystalline forms, enantiomers, isomers, metabolites, physiologically acceptable prodrugs may be formulated as syrups, elixirs, concentrated drops or suspensions having a pharmaceutically acceptable vehicle such as a mix of ethanol, glycerol, propylene glycol, and/or polyethylene glycol, among others, carboxyl methyl cellulose or other thickening agents; it may contain coloring, flavor, sweetening (sucralose, aspartame, cyclamate, *stevia*) and preservation (parabens, benzoates) agents. These liquid doses may be prepared on the basis of reconstituting powdered pharmaceutical compositions with a suitable diluent prior to being used.

For parenteral administration, the general formula III compound (JM-20) or its salts, hydrates, crystalline forms, enantiomers, isomers, metabolites, physiologically acceptable prodrugs may be formulated as injectable solutions. These solutions may contain stabilizing, preserving and/or buffer ingredients.

In this invention, the active pharmaceutical ingredient is in a 69% ethanol solution, benzoic alcohol, propylene glycol, benzoic acid, sodium benzoate, sodium hydroxide, water for injection; other excipients may also be used such as polyethylene glycol 400, sodium citrate and citric acid.

Solutions for parenteral administration which contain the general formula III compound (JM 20) or its salts, hydrates, crystalline forms, enantiomers, isomers, metabolites, physiologically acceptable prodrugs may also be prepared by reconstitution of a dry pharmaceutical composition (lyophilized) with a suitable diluent prior to being used including the use of auxiliary substances such as monitol, polysorbate 80, sodium chloride, and others.

For subdermal administration the general formula III compound (JM 20) or its salts, hydrates, crystalline forms, enantiomers, isomers, metabolites, physiologically acceptable prodrugs may be dosed as implants using auxiliary substances such as silicone elastomers and anhydrate colloidal silicone even though for the putting together of the pellet other pharmaceutical use polymers may be used.

For transdermal administration, the general formula III compound (JM 20) or its salts, hydrates, crystalline forms, enantiomers, isomers, metabolites, physiologically acceptable prodrugs may be formulated as patches; in this case the active pharmaceutical ingredient is contained in a support of acrylic copolymer, ethanol, light liquid paraffin, isopropyl palmitate, polyethylene terephthalate, ethylene vinyl acetate solution and a layer of silicone in the inside of the detachable sheet (with a nominal liberation rate of 15 mg/day, on a surface area of 12.75 $cm^2$)

REALIZATION EXAMPLES

This example demonstrate the synthesis of the 4-(2'nitrophenyl)-5-carbonylethoxy-2-methyl-3,4-dihydro-2(1H) pyridine (I) and the corresponding o-chloroformyl 1,4-dihydropyridine derivative (II) which are part of the synthetic intermediates required to obtain the final products of type III.

Compound II is obtained on the basis of the transformation of I via phosphorus oxychloride, in dry dimethyl formamide, whose mix is subsequently added in the proportion of 3 to 9 times to a dissolution of I in dichloromethane or chloroform and is agitated at a temperature between 20-60° C. for 15-20 hours (FIG. 1).

The resulting product is then submitted to basic hydrolysis, with later extraction with chloroform or dichloromethane, purification by means of washing and drying.

Compound I is obtained by a multi-component reaction in one single step, where we mix in equimolar quantities 2-nitrobenzene aldehyde, Meldrum's acid, ethyl acetoacetate and ammonium acetate, in acetic acid as dissolvent and undergoing reflux reaction during 7-10 hours. After that time, the mix is poured over water and the resulting precipitate is purified by means of ethanol recrystallization.

This Example Demonstrate the Synthesis of the Compound III.

The Compound IIa or IIb previously obtained undergoes a reaction with orthophenylenediamine in absolute ethanol to obtain Compound III (JM-20) which may be prepared forming different salts, depending on the conditions of reagents used.

Obtaining Compound III from IIa

Figure 2:
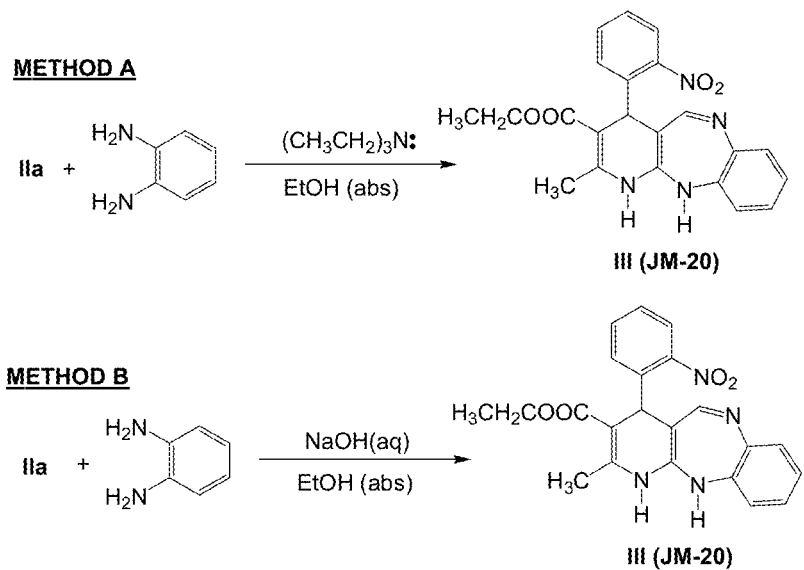
FIG. 2. Synthesis of compound III from IIa.

To obtain Compound III (JM-20) we start from an ethanol solution of Compound IIa and we add equimolar amounts of orthophenylenediamine, in absolute ethanol as dissolvent, with agitation. Equimolar amounts or greater (1-2 equivalents) of triethylamine (FIG. 2, Method A) are added to the reaction mix, maintaining agitation or adding sufficient amounts (1-1.5 equivalents) of sodium hydroxide dissolution by controlled dripping and by continuously agitating the reaction mix (FIG. 2, Method B).

Obtaining Compound III from IIb

Figure 3:
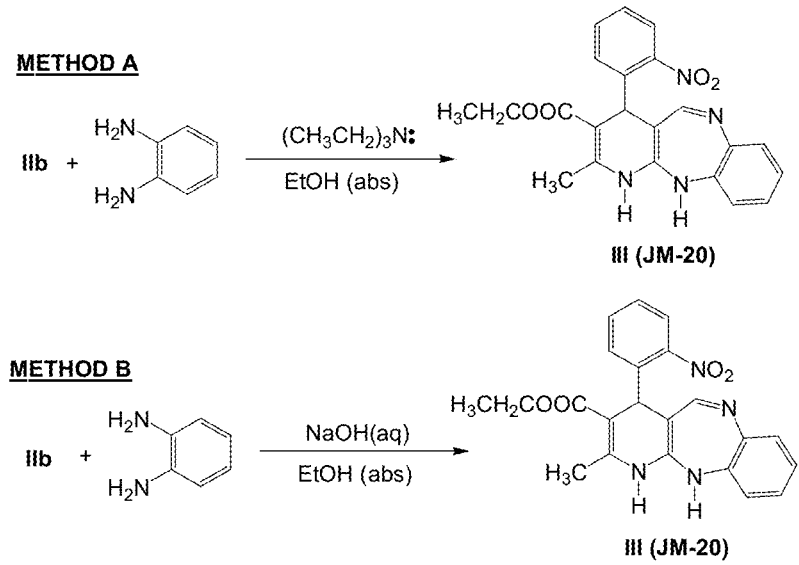
FIG. 3. Synthesis of compound III from IIb.

To obtain Compound III (JM-20), we start with Compound IIb in ethanol dissolution and we add equimolar amounts of orthophenylenediamine, in absolute ethanol as dissolvent, with agitation. Equimolar amounts or greater (1-2 equivalents) of triethylamine (FIG. 3, Method A) are added to the reaction mix, maintaining agitation or adding sufficient amounts (1-1.5 equivalents) of a sodium hydroxide dissolution by controlled dripping and by continuously agitating the reaction mix (FIG. 3, Method B).

Figure 4:
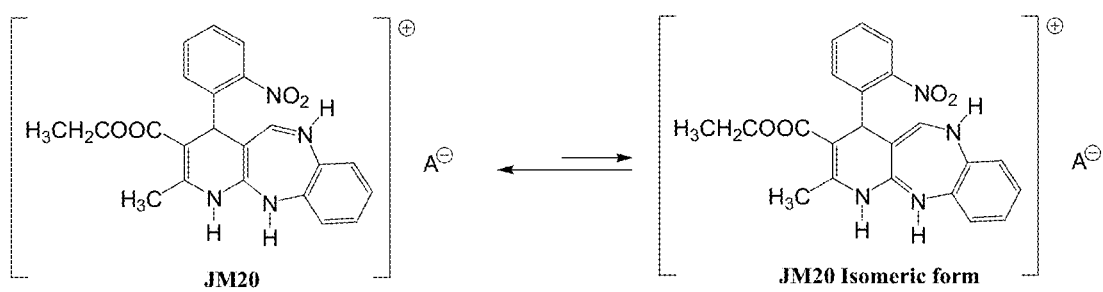
FIG. 4. Isomeric form of JM20.

Compound JM20's isomer structure is shown in FIG. 4.

Obtaining Compound III as Halohydrate-Type Salts

Figure 5:
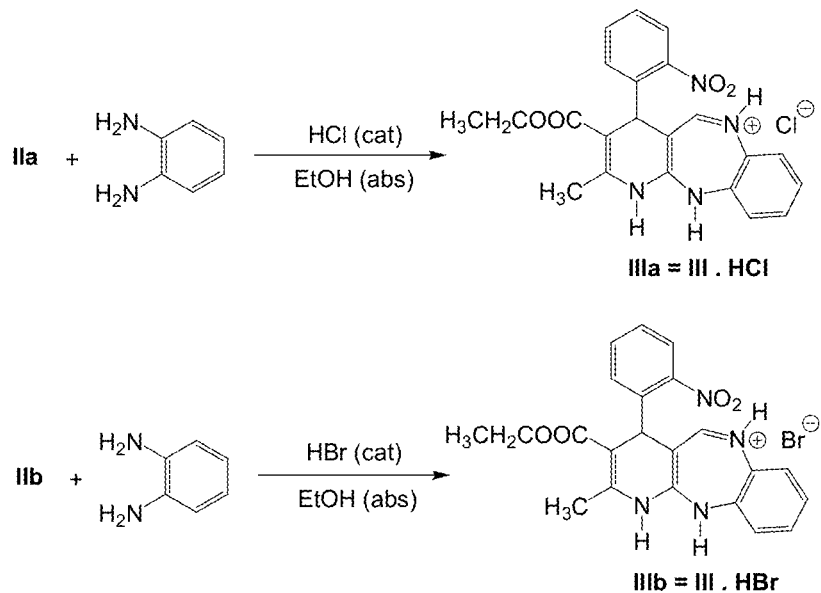
FIG. 5. Obtaining compound III and its Halohydrates
FIG. 6. Obtaining fumarate salt from JM-20 (IIIc).

The corresponding chlorhydrate or bromohydrate salts of III (halohydrates of JM-20) are obtained from IIa or IIb respectively with or without the use of a catalyzer. When the corresponding hydracid is added in suitable catalytic amounts (5-25% mol), catalysis process occurs which decreases the reaction time and slightly increases the reaction yield (FIG. 5).

JM20 (IIIa) chlorhydrate is properly obtained from IIa, and when suitable amounts of HCl are added, reaction catalysis occurs. The JM-20 Compound may also be obtained as bromohydrate (IIIb) from IIb (FIG. 5) with the characteristic of the bromide being a better salient group that chloride, the reaction of intramolecular nucleophilic substitution is facilitated, resulting in a rapid and efficient reaction to obtain JM-20 as a bromohydrate.

Obtaining Compound III as Fumurate Salt

Figure 6:
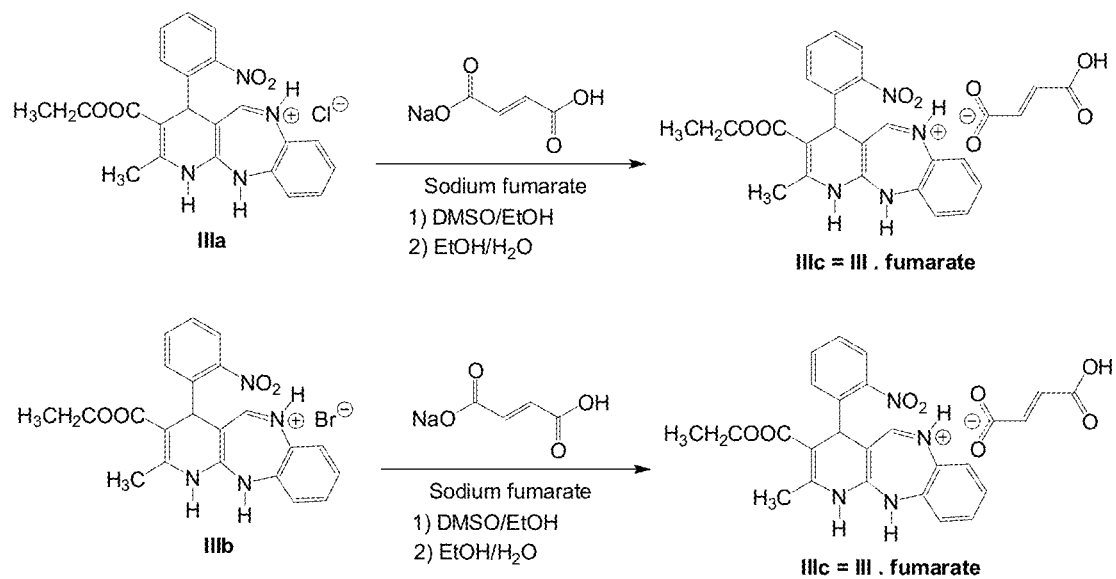

JM-20 (IIIc) fumurate salt is obtained from the chlorhydrate or bromohydrate of III upon adding monosodium fumurate to a IIIa or IIIb dissolution, with magnetic agitation for 2-5 hours (FIG. 6) and its subsequent precipitation upon adding ethanol in suitable amounts.

The precipitate corresponding to the IIIc fumurate is suitably filtered and washed, purified and subsequently placed in a controlled-temperature dryer at reduced pressure.

Obtaining Compound III in Phosphate Salt Form

Figure 7:
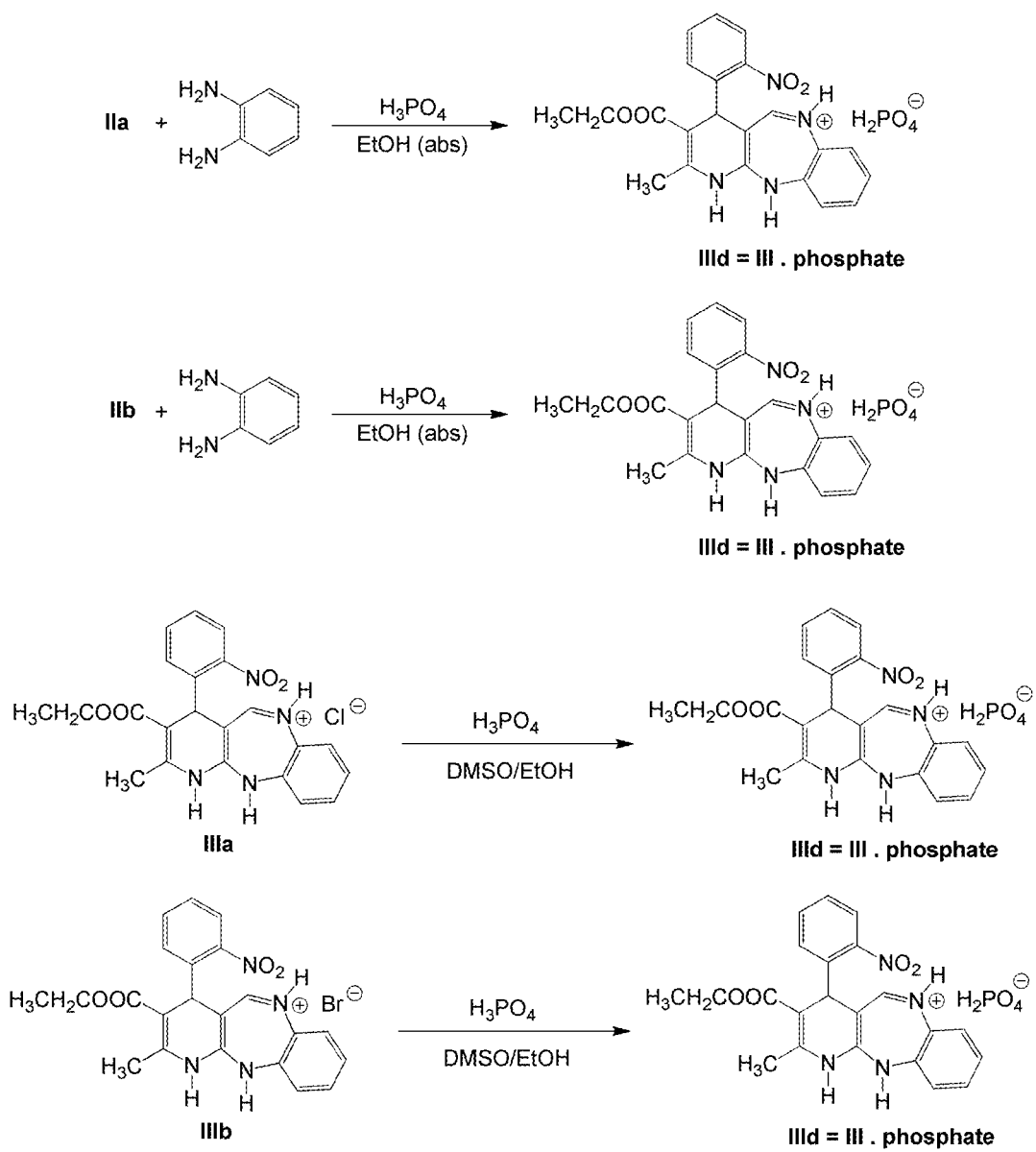
FIG. 7. Obtaining phosphate salt from JM-20 (IIId).

JM-20 (IIId) phosphate salt may be obtained by a process similar to the one above, from IIa or IIb, by adding equimolar amounts of phosphoric acid at the start of the reaction or by adding phosphoric acid to IIIa or IIIb in ethanol solution, with agitation (FIG. 7).

Obtaining Compound III in Sulphate Salt Form

Figure 8:
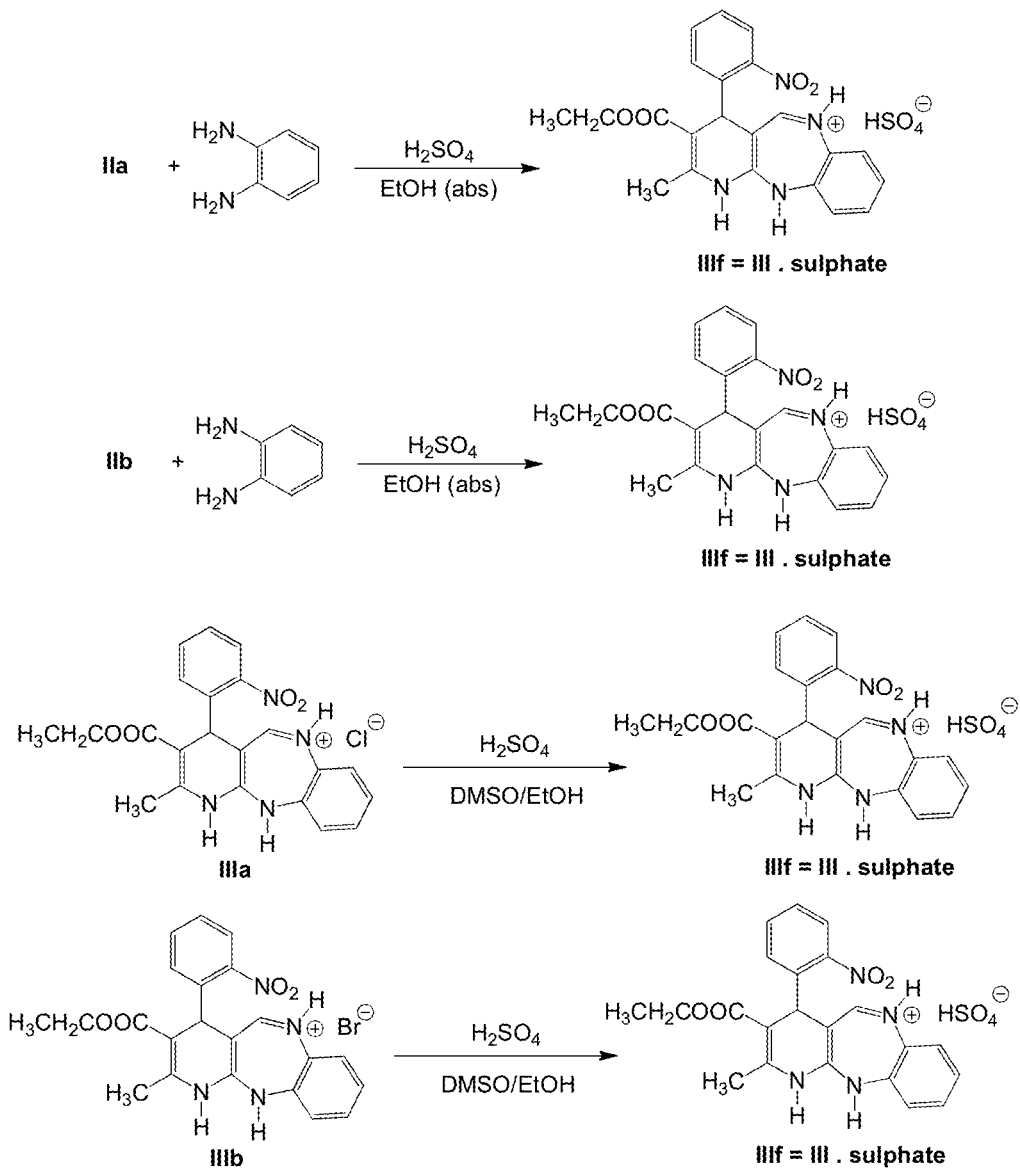
FIG. 8. Obtaining sulfate salt from JM-20 (IIIf).

JM-20 (IIIf) sulphate may be obtained from IIa or IIb or on the basis of IIIa or IIIb halohydrates, as shown in FIG. 8.

Obtaining Tablet-Form Formulation

Each 120.00 mg tablet contains:

| Component | Amount | Function |
|---|---|---|
| JM 20 | 40.00 mg | Active principle |
| Cornstarch | 23.00 mg | Desintegrater |
| Polyvinyl pyrrolidone K-25 | 4.00 mg | Agglutinin |

-continued

| Component | Amount | Function |
|---|---|---|
| Monohydrated lactose | 50.50 mg | Filler |
| Magnesium stearate | 1.50 mg | Lubricant |
| Colloidal silicone dioxide | 1.00 mg | Lubricant |
| Class C Ethanol* | 12.00 μl | Solvent |
| Deionized water* | 12.00 μl | Solvent |

*Evaporates during the drying process.

Brief Description of the Technological Process:
1. Sift the active principle, cornstarch and lactose through a 20-mesh.
2. Weigh all the components of the formulation according to amounts established in the formula.
3. For the agglutinin solution, pour the mixture of water and Class C ethyl alcohol into a metal container with steam jacket, add the polyvinyl pyrrolidone and shake until completely dissolved.
4. Load the mixer with the active principle, cornstarch and lactose (components of the internal phase). Mix for 15 min.
5. Add the agglutinin solution slowly using the peristaltic pump, completing the degree of moistness required using water and Class C ethyl alcohol (1:1) if necessary. Grind in a mill at low speed.
6. Dry the granulate in a fluidized bed. After 10 minutes take a representative sample of granulate, degranulate and test its residual humidity; said humidity should register between 0.8 and 1.2%.
7. Mix the dry granulate with lubricants for 10 min.
8. In a high-speed rotating machine, compress the mix using flat, beveled and grooved 6.4 mm diameter (¼ PBR) dies to obtain tablets having the following parameters:
   Mass: 120.0 mg±10%
   Height: 2.6±0.10 mm
   Hardness: 4.0±1 KgF
   Friability: less than 1%

Obtaining Formulation for Oral Drop Form

Every mL (20 drops) contains:

| Component | Amount | Function |
|---|---|---|
| JM-20 | 40.0 mg | Active principle |
| Propylene glycol | 300.0 mg | Vehicle dissolvent |
| Kollidon 25 | 160.0 mg | Viscosity agent |
| Sodium saccharine | 12.5 mg | Sweetener |
| Ponceau S. acid red | 0.05 mg | Color |
| Citric acid | 5.535 mg | pH stabilizer |
| Dehydrated sodium citrate | 20.0 mg | pH stabilizer |
| Ethyl alcohol | 100.0 mg | Vehicle dissolvent |
| Methyl paraben | 1.8 mg | Preservative a.m. |
| Propyl paraben | 0.2 mg | Preservative a.m. |
| Liquid strawberry flavor (soluble) | 20.0 mg | Flavoring |
| Purified water c.s.p. | 1.0 mL | Vehicle |

Brief Description of the Technological Process:
1. Measure the pH and the conductivity of the purified water at the moment of manufacturing the product.
2. Pour propylene glycol into the reactor.
3. Dissolve sodium saccharin into purified water in an auxiliary stainless steel recipient with the proper capacity.
4. Incorporate Kollidon 25, scattering it little by little, agitating for at least 30 minutes until totally dispersed.
5. Agitate and apply heat to the preparation, keeping the temperature between 40-50° C. for 30 minutes.
6. Incorporate the active principle to the results of the previous step in small portions, keeping constant agitation for 30 minutes.

7. Remove heat and wait for the preparation to attain room temperature: 30±2° C.
8. Dissolve the methyl paraben and propylene glycol in Class C ethyl alcohol in an auxiliary glass or stainless steel recipient with the proper capacity, constantly agitating it until totally dissolved.
9. To the results of the previous step, add soluble liquid strawberry flavor and agitate until completely homogenous.
10. Incorporate the results of the previous step slowly into the reactor tank, constantly and strongly agitating it.
11. Dissolve the citric acid and dehydrated sodium citrate in a glass or stainless steel recipient, with the proper capacity, agitating it after every addition until completely dissolved.
12. Slowly incorporate the results of the previous step to the reactor tank, constantly and strongly agitating it.
13. Dissolve Ponceau S. acid red in purified water in a glass or stainless steel recipient having the right capacity, agitating it until totally dissolved and incorporating the preparation.
14. Skim the prearranged volume with water. Agitate until uniform.
15. Test that the pH is maintained at the 4.0-6.0 interval.
16. Do a final filtering; test organoleptic characteristics.
17. Bottle the final preparation in amber glass bottles×15 mL, with 15.0±1.0 mL of the solution, properly lidded, using tops having drip reducers for oily products.

Obtaining Injectable Formulation:
Every bulb (2 mL) of JM-20 contains:

| Component | every mL contains | Amount per Dose Unit | Function |
| --- | --- | --- | --- |
| JM-20 | 5.0 mg | 10.0 mg | Active principle |
| Cremofor ELP | 527.0 mg | 1054.0 mg | Vehicle |
| Chlorhydric acid 1N c.s.p | — | — | Nonadjust for pH |
| Dehydrated alcohol c.s.p | 1.0 mL | 2.0 mL | solvent |
| *Nitrogen cs | — | — | |

1. Check that the reactor is completely dry after being sterilized; if not, rinse it out with dehydrated alcohol.
2. Prepare a solution of 1 N chlorhydric acid to adjust the pH.
3. Add one part of Cremofor ELP and dehydrated alcohol to the reactor. Mix at 420 rpm.
4. Weigh the active principle and add portions of dehydrated alcohol to the beaker containing it; disperse it with the glass stirrer and add to the reactor; repeat this operation until all the active principle has been swept away and all the dehydrated alcohol has been used up.
5. Keep up the agitation in the reactor for 60 minutes at 420 rpm until the active principle is totally dissolved.
6. Add the rest of the Cremofor ELP, sweeping the remainder with dehydrated alcohol, agitating it for 10 minutes at 420 rpm.
7. Determine the solution's pH and adjust it with 1N chlorhydric acid, between 5.0-6.0.
8. Complete the solution's volume by adding dehydrated alcohol. Agitate for 5 minutes at 420 rpm.
9. Take 10 mL of the solution and send it to the laboratory for process control (assessment and pH)
10. Check the correct setting-up of the filling and nitrogenation systems.
11. Run the integrity test of the Sartobran P MidiCaps filter, (0.45+0.2 µm) porosity with dehydrated alcohol.
12. Once the process control is finished, pressurize the reactor using nitrogen (0.7-1.0 bar) to propel the solution through the 0.45 µm+0.2 µm porosity Sartobran P filter cartridge. Fill and seal the bulbs, making doses of 2.2 mL of the solution.

Memory Studies in Dementia Models

Reagents

All reagents were bought from Sigma-Aldrich (St. Louis, Mo., USA). JM-20 was administered in sufficient amounts for the studies proposed by the organic synthesis laboratory at the Faculty of Chemistry of the University of Havana.

For the different studies JM-20 was suspended in carboxymethyl cellulose (CMC) 0.05% and administered orally. Scopolamine bromide was dissolved in the 0.9% saline solution and administered intraperitoneally (1 mg/kg, 4 mL/Kg of weight). Aluminum chloride was dissolved in common drinking water for the experimental subjects and administered orally in a 500 mg/Kg peso dose, in chronic form for one month and while behavioral studies were conducted. Beta amyloid peptides (25-35) were oligomerized and made soluble according to the manufacturer's norms and administered via intracerebroventricular means at 100 pmols in 5 uL, into the right cerebral hemisphere.

Experiment Animals. Ethical Considerations.

In vivo experiments corresponding to the scopolamine and aluminum model used Wistar rats (males, 230-260 g), while in vivo experiments corresponding to the beta amyloid model used OF-1 mice (males, 25-30 g). All the animals came from the National Laboratory Animal Production Center (CENPALAB, Mayabeque, Cuba) and after their arrival they underwent adaptation to laboratory conditions for 7 days. They were kept under alternating 12-hour cycles of light and dark, at controlled temperatures (22±2° C.), 45-55% relative humidity and they were given water and food freely on demand. All behavioral studies were carried out between 09:00 and 17:00 under controlled conditions of light and noise levels. All procedures with animals reported in this study were done according to criteria approved by international committees for the care of laboratory animals and in accordance with national regulations established for experiments with animals.

Experiment Design

Protocol 1: Evaluation of the JM-20 Effect on Memory Loss Induced by Scopolamine We investigated the protector effect of three doses of JM-20 (2, 4 and 8 mg/kg) on the processes of the acquisition and consolidation of short and long-term memory, affected by the acute intraperitoneal administration of scopolamine. For this purpose, JM-20 was administered prior to the affectation or the process of acquisition and consolidation of memory, both short and long-term memory, in four independent tests.

In each test we formed 6 experimental groups of subjects chosen at random (n=10, per group): healthy control group (CMC and saline); JM-20 non-damaged group (JM-20 8 mg/kg); scopolamine group (CMC and scopolamine 1 mg/kg); JM-20-scopolamine (JM-20 2 mg/kg and scopolamine 1 mg/kg), (JM-20 4 mg/kg and scopolamine 1 mg/kg) and (JM-20 8 mg/kg and scopolamine 1 mg/kg) groups. The effect on memory was assessed by the test of recognizing novel objects and the forced alternation Y-maze test, using experiment designs suitable for the independent study of the process of acquiring and consolidating short and long-term memory.

At the end of the behavioral studies, we conducted different in vivo studies on the basis of cerebral tissue. We studied the effect of JM-20 on different oxidative stress markers, mitochondrial function, levels of activity of the acetylcholinesterase AchE enzyme and the histological parameters of neuronal and axonal viability in cerebral regions closely involved in the processes of memory and learning.

Protocol 2: Evaluation of the JM-20 Effect on Memory Loss Induced by Aluminum Chloride We investigated the protector effect of two doses of JM-20 (2 and 8 mg/kg) on different types of memory affected by acute intraperitoneal administration of scopolamine. For this purpose JM-20 was administered from the 15 days following the start of administering aluminum chloride (500 mg/kg) until the end of the behavioral studies. We evaluated the effect of JM-20 and aluminum chloride on three types of memory: spatial memory by the Morris Water Maze test and the T-maze test; recognition of novelty by the novel object recognition test; and emotional-associative memory by the passive avoidance test.

5 experimental groups of randomly selected subjects were formed (n=10, per group): healthy control group (CMC and water); undamaged JM-20-group (JM-20 8 mg/kg and water); aluminum (CMC and aluminum chloride 500 mg/kg) group; JM-20-aluminum (JM-20 2 mg/kg and aluminum 500 mg/kg), and (JM-20 8 mg/kg and aluminum 500 mg/kg) groups.

Upon the conclusion of behavioral studies, we conducted different in vivo studies on cerebral tissue. We studied the effect of JM-20 on different oxidative stress markers, mitochondrial functionality and the levels of activity of the acetylcholinesterase AchE enzyme Protocol 3: Evaluation of the JM-20 Effect on Damage Induced by Beta Amyloid 25-35 Peptide Oligomers Initially we assessed the effect of JM-20 on the cellular viability of a line of PC12 cells submitted to a 1 uM concentration of beta amyloid 25-25 peptide oligomers. This in vitro test evaluated the effect of 3 concentrations of JM-20 (3.125, 6.25 and 12.5 uM) made soluble in dimethylsulfoxide (DMSO). 6 experiment groups were formed: non-treated control group (NT); vehicle group (DMSO); beta amyloid group (A$\beta$ 1 $\mu$M); JM-20-beta amyloid (JM-20 3.125+A$\beta$ 1 $\mu$M), (JM-20 6.25+A$\beta$ 1 $\mu$M) and (JM-20 12.5+A$\beta$ 1 $\mu$M) groups.

Subsequently we conducted in vivo studies on OF-1 mice. We assessed the effect of JM-20 on memory loss induced by beta amyloid oligomers administered 7 days after the intracerebroventricular administration of A$\beta$ (100 pmols) during 10 days, orally in 10 and 30 mg/kg weight doses. We formed 5 experiment groups: healthy control group (Sham); undamaged JM-20 group (Sham+JM-20 30 mg/kg); beta amyloid group (A$\beta$ 100 pmol+CMC); JM-20-beta amyloid (JM-20 10 mg/kg+A$\beta$ 100 pmol) and (JM-20 30 mg/kg+A$\beta$ 100 pmol) groups.

Behavioral Studies

Y-Maze. Spontaneous Alternation

The effect of JM-20 on spatial memory was evaluated by the Y-maze forced alternation test (20). The maze was built of plastic with three arms (55×20×20 cm) at an angle of 120° on a central platform. The test was run in two sessions. In a first learning phase we carried out the training phase during which each rat was placed on the central platform and allowed to freely explore the arms (A and C) of the maze for 10 minutes while the third arm (B) was kept closed off. Entries into each arm were considered as entries into the four extremities inside any of the arms. The sequence of entries into the arms for 10 minutes was video-recorded to be analyzed later. The evaluation phase consisted in allowing the rats to freely explore the Y-maze arms for 5 minutes including the one that had been previously closed off. The sequence of entries into the arms was taped for 5 minutes for subsequent analysis. This test assessed the number of entries into the new arm (B), where the percentage of entries into this arm is directly proportional to better memory in the animals being studied. The percentage of correct entries into Arm B was calculated on the basis of the proportion of alternations carried out from the total possible alternations, as shown in the following equation: % of correct entries= (number of entries into B)/(total of entries into the three arms)×100. After each test, the maze was cleaned with a 40% ethanol solution to reduce the existence of olfactory clues.

Object Recognition

The effect of JM-20 on memory of recognized novel objects was assessed by the object recognition test. This test was conducted in an open field on 2 successive days. On the first day the animals were adapted to the field, letting them explore the box for 3 minutes, in 2 sections. On the second day, training was carried out with learning assessment by 2 stages of 5 minutes each, hereinafter treated as Training (E) and Test Phase (P), respectively. During the E Stage, rats were presented with 2 identical objects, called Familiar (F) Objects. After 30 minutes, P Stage started and rats were exposed to the Familiar Object F and a Novel Object (N). Tests were recorded to analyze the exploration of the objects, defined by the time of exploration taken by each animal for each object. The rates of discrimination between objects F and N were calculated as $ID=(N-F)/(N+F)$.

Morris Water Maze

The Morris Water Maze was conducted as described by Vorhees y Williams (21) with a few modifications, in a circular tank (1.52 m in diameter, 0.60 m in depth). 5 days of training took place, 4 sections per day and Day 6 was for learning evaluation. The animals were to learn how to locate a submerged platform, fixed in an unchangeable position, during all the training sections. Several external clues were placed and kept in a fixed position during the entire experiment. At each training session animals were placed into the water, facing the wall of the tank, at one of the 4 exit sites, until they found the platform within a maximum time of 1 minute. On assessment day, the platform was removed. We quantified the latency of escape (the time the animal took in finding the platform) in training trials, the time the animal remained in the quadrant of the platform during the test for learning evaluation and the distance covered until the platform site was found.

Passive Avoidance

The passive avoidance test was conducted based on the methodology described by Kohara and collaborators (22) with a few modifications. We used passive avoidance equipment (UGO Basile) consisting of 2 chambers, one which was lit (30×30×30 cm) and one which was dark (10×20×12 cm), connected by an access door in the form of a guillotine. The dark chamber was equipped with an electrical circuit.

The test was conducted in 2 stages on 2 consecutive days. On the first day, each rat was placed in the lighted chamber for 10 seconds, then the door between the chambers was opened and the rat was allowed to freely explore during a maximum time of 90 seconds. Once the rat had entered the dark chamber, the access door was closed and the rat received an electric charge of 1 mA for 5 seconds. On the second day, the latency of entry into the dark chamber was measured in a maximum time of 300 seconds.

Mitochondrial Functionality Studies
Isolating Cerebral Mitochondria

Mitochondria were isolated by differential centrifuge. Animals were sacrificed by decapitation and their brains were immediately removed, cut into 50 mL isolation buffer containing sucrose 75 mmol/L, EGTA 1 mmol/L, manitol 225 mmol/L, BSA 0.1% and HEPES-KOH 10 mmol/L, pH 7.2, a 4° C., and homogenized in a Potter-Elvehjen. The suspension thereby obtained was centrifuged at 2000 g for 3 minutes and the floating matter was centrifuged at 12000 g for 8 minutes. The sediment was re-suspended in 10 mL of isolation buffer also containing 20 uL digitonin at 10% and this was centrifuged at 12000 g for 10 minutes. The mitochondrial sediment was suspended in isolation buffer without EGTA, and it was centrifuged at 12000 g for 10 minutes, the floating matter was disposed of and it was gently washed with isolation buffer without EGTA. The microLowry method was used to determine the concentration of proteins using bovine serum albumin as the standard pattern (Mirandola et al., 2010). Mitochondria were incubated in a medium of KCl 130 mmol/L, $MgCl_2$ 1 mmol/L and HEPES-KOH, phosphate 2 mmol/L, pH 7.4. Mitochondria (1 mg protein/mL) were energized with 5 mmol/L and rotenone 2.5 μmol/L potassium succinate.

Mitochondrial Membrane Potential

Mitochondrial membrane potential was determined using a POLARstar Omega (Germany) fluorescence spectrophotometer and using the fluorescent marker of safranin O (10 μM) in a POLARstar Omega (Germany) fluorescence spectrophotometer at 495/586 nm (excitation/emission).

Mitochondrial Swelling

Mitochondrial swelling was monitored by the decrease in apparent absorbency at 540 nm of the suspension of mitochondria incubated in a standard medium, in the presence of $Ca^{2+}$ 200 μmol/L and using a POLARstar Omega (Germany) fluorescence spectrophotometer.

Production of Reactive Oxygen Species

Reactive Oxygen Species (ROS) were determined by spectrofluorometry using Amplex red (Molecular Probes, OR, Eugene) as the fluorescent marker and 1 UI/ml of horseradish peroxidase at 563/587 nm (excitation/emission).

Preparation of Cerebral Tissue for Enzyme and Redox Status Tests

Rats were sacrificed by decapitation; their brains were removed and quickly dissected in order to separate 2 regions, the hippocampus and the prefrontal cortex of both cerebral hemispheres (23). These regions were homogenized in sodium phosphate buffer solution (0.1 mM, pH 7.4: NaCl 0.13 M, KCl 0.0027 M, $KH_2PO_4$ 136.04 M, $Na_2HPO_4$ 0.0016 M) in a proportion of 1:10 (p: v), and they were centrifuged at 6,000 g for 20 minutes in an Eppendorf Centrifuge (Germany, 5424R). The proportions of the homogenate of the cerebral structures were preserved at −80° C. until they were used. Their protein concentration was determined by the Lowry Method (24) in a POLARstar Omega (Germany), using bovine serum albumin as reference.

Acetylcholinesterase (AChE) Activity

Activity of the AChE enzyme present in the homogenate of the extracted hippocampus and prefrontal cortexes was measured spectrophotometrically using the method described by Ellman (25) with slight modifications (26). The test took place on a 96-well sheet with a final volume of 200 μL. The reaction medium contained 140 μL of Ellman's reagent, 50 μL of homogenate and 10 μL of 20 mM iodate acetyltiocolin (AcSCh) solution and it was incubated for 1 minute at 37° C. Absorbency was read at 405 nm for 20 minutes with 1 minute intervals in a POLARstar Omega (Germany) fluorescence spectrophotometer. Enzyme activity was calculated and expressed as pmols of hydrolyzed (AcSCh) in one minute per protein mg.

Study of Redox Status and Oxidative Damage Parameters
Superoxide Dismutase (SOD) Activity SOD enzyme activity was determined using the pyrogallol oxidation method (27). The reagent mixture was composed of a solution of 2.8 mL of Tris 0.2 M-HCl 0.2 M (pH 8.2), 0.05 mL EDTA 60 mM, 0.1 mL de homogenate and 0.05 mL of pyrogallol solution 7.37 mM. Absorbency was read at 420 nm for 1 minute in a POLARstar Omega (Germany) fluorescence spectrophotometer. The results were expressed as units of enzyme activity per mg of protein, considering 1 unit of enzyme activity as the amount of enzyme catalyzing the conversion of 1 μmol of substrate in one minute.

Catalase (CAT) Activity

CAT enzyme activity was determined on the basis of the decomposition of hydrogen peroxide ($H_2O_2$) (28). The reagent mixture was composed of 0.9 mL of phosphate buffer (pH 7.0), 0.1 mL of cerebral tissue homogenate and 0.5 mL of $H_2O_2$ (50 mM). Absorbency was read at 240 nm, at 10 and 70 seconds, in a POLARstar Omega (Germany) fluorescence spectrophotometer. The results were expressed as μmols of $H_2O_2$ decomposed per minute per mg protein.

Reduced Glutation (GSH) Levels

GSH levels were estimated following methodology described by Ellman (29), with some modifications. In a tray we added 0.375 mL of phosphate buffer (50 mM, pH 8.0), 0.1 mL of homogenate and 0.025 mL of a solution of 5.5'-ditio-bis-nitrobenzoic acid (DTNB)/acetone (0.6 mM). Absorbency was read at 412 nm, in a POLARstar Omega (Germany) fluorescence spectrophotometer. The results were calculated using the coefficient of molar extinction of the cromofor formed $(1.36 \times 10^4 \, (mol/L)^{-1} \, cm^{-1}$. The results were expressed as GSH nmols per mg of protein.

Lipid Peroxidation Levels

Lipid peroxidation levels were quantified by detecting malondialdehyde (MDA) formed from the reaction with tiobarbituric acid (30). The reagent medium was formed by 350 μL of a mix of trichloroacetic acid: tiobarbituric uric acid: chlorhydric acid, 100 μL of cerebral tissue homogenate and 50 μL of di-ter-butylhydroxytoluene (BHT). The mixture was homogenized in a TALBOYS (USA) vibro-agitator and was placed for 5 minutes in a Grant OLS200 (USA) thermostat water bath at 100° C. Subsequently it was centrifuged at 3,000 rpm for 10 minutes in an Eppendorf Centrifuge (Germany, 5424R). The MDA formed as a product of the lipid peroxidation in the cerebral tissue reacts with the tiobarbituric uric acid and yields a colored compound which was determined by spectrophotometry at 535 nm in a POLARstar Omega (Germany) fluorescence spectrophotometer. MDA concentration was calculated taking into account the coefficient of molar extinction of the colored compound formed $(1.56 \times 10^5 \, M^{-1} \, cm^{-1})$ and depending on the following equation:

$$C = \frac{D.O}{1.56} \times 10^4 \, nM$$

where C is the MDA concentration to be determined and D.O is the absorbency detected. The results were expressed as MDA nanomols per mg of protein.

Histological Study

The histological evaluation of the lesions caused by acute intraperitoneal administration of scopolamine was carried out on regions of the hippocampus and prefrontal cortex. We used the Paxinos and Watson Atlas (31) with the anatomic description of the rat brain to identify each cerebral region and they were processed for tincture of hematoxilin and eosin (HE) in crown sections 4 µm thick, always taking the first three cuts of each region. Both hemispheres were observed in a Leica (Microsystems, Germany) optical microscope. Neuronal damage was evaluated in the CA1, CA2, CA3 zones and the hippocampus dentate gyrus and atrophy, nuclear pyknosis, dark cytoplasm coloration or the absence of neurons were considered as degeneration markers. In addition we calculated axonal damage specifically based on the appearance of partially or totally demyelinated axons as well as axon atrophy and it was expressed as a percentage of the total axons present in each slide or each region studied. Carrying out the analysis of histological damage at the level of the prefrontal cortex, we counted the average number of neurons and axons affected in the three fixed areas of each cerebral hemisphere and it was expressed as a percentage of damaged neurons/axons as compared to the total in each area.

Statistical Analysis

For statistical processing and the analysis of results obtained, we used the GraphPad Prism 5.0 (GraphPad Software Inc., USA.) program. Data was expressed as the mean±EEM (standard mean error) and we checked its normality and homoscedasticity. Simple classification variance analysis (ANOVA) was carried out, followed by the Tukey Test for multiple comparisons to make comparisons between the different experimental groups. A value of $p<0.05$ was considered to be statistically significant.

Results are shown in FIGS. 9 to 14.

Figure 9:
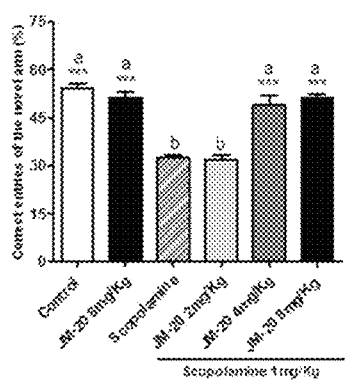
FIG. 9: Effects of JM-20 on short and long term spatial memory, particularly in the processes of acquisition and consolidation. Data is expressed as mean±SD (n=7, per group) of the percentage of spontaneous alternation. For statistical analysis, a multiple comparison ANOVA and Tukey test were performed. Different letters differ from each other for $p<0.05$.
Figure 9:
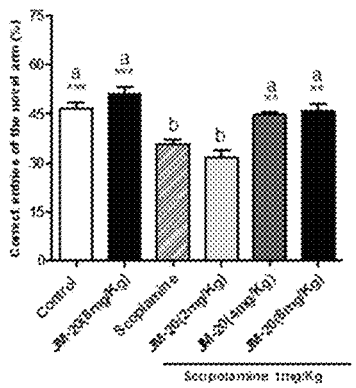
Figure 9:
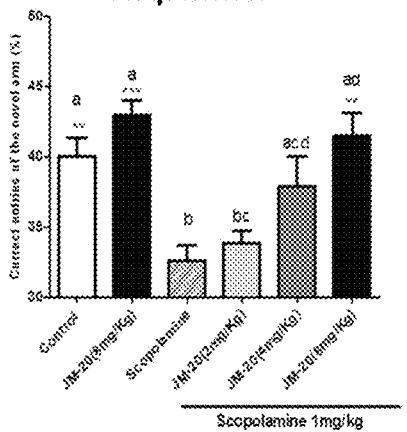
Figure 9:
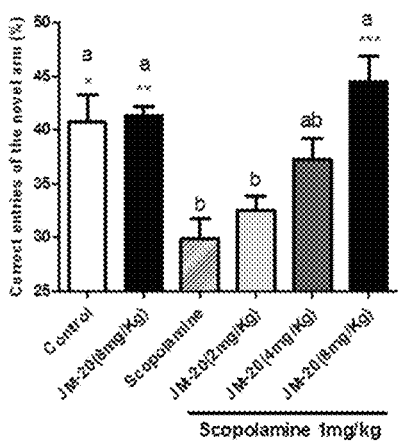

FIG. 9 shows the effects of JM-20 on short and long term spatial memory, particularly in the processes of acquisition and consolidation. Data is expressed as the mean±DE (n=7, per group) of the percentage of spontaneous alternation. For the statistical analysis we carried out ANOVA and Tukey multiple comparison tests. Different letters differentiate amongst themselves for $p<0.05$.

Figure 10:
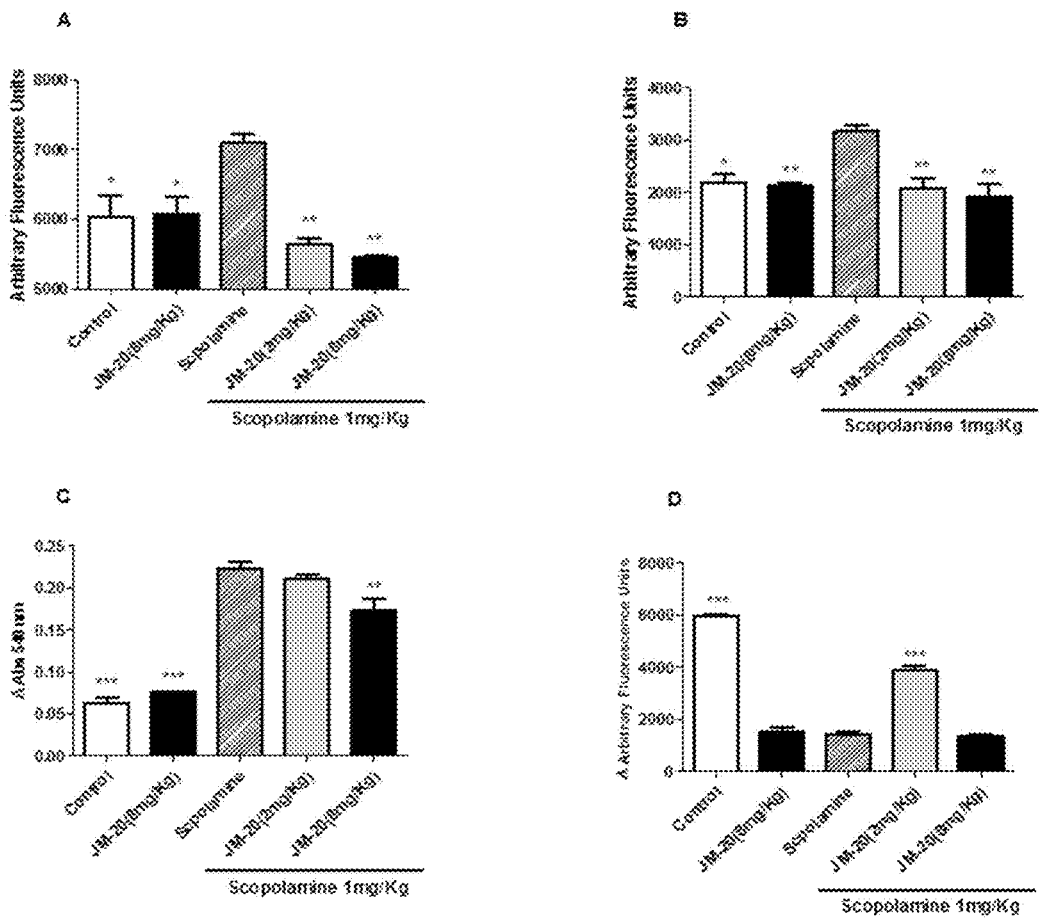
FIG. 10: Effects of JM-20 on the mitochondrial dysfunction of cerebral tissue in rats treated with scopolamine. after completing short-term memory studies. The different doses of JM-20 were administered orally 1 h before administration of scopolamine. Brain mitochondria were isolated 1 h after administration of scopolamine and the membrane potential (A), $H_2O_2$ generation (B), mitochondrial swelling (C) and calcium influx to the mitochondria (D) were evaluated. Bars represent the mean±SEM (n=10). Different letters show differences between groups: $p<0.05$, by ANOVA and Tukey's post hoc. (A): *, $p=0.0009$, (B): , $p=0.0034$ relative to the vehicle/scopolamine group 1 mg/Kg, by ANOVA and Tukey's post hoc.

FIG. 10 shows the effects of JM-20 on the mitochondrial dysfunction of cerebral tissue in rats treated with scopolamine, after completion of short-term memory studies. The different doses of JM-20 were administered orally 1 hour prior to the administration of the scopolamine. Brain mitochondria were isolated 1 hour after the administration of the scopolamine and we assessed membrane potential (A), $H_2O_2$ generation (B), mitochondrial swelling (C) and calcium influx to the mitochondria (D). The bars represent the mean±EEM (n=10). Different letters show the differences between groups: $p<0.05$, by ANOVA and post hoc Tukey. (A): *, $p=0.0009$, (B): , $p=0.0034$ regarding the vehicle/scopolamine 1 mg/Kg group, by ANOVA and post hoc Tukey group.

Figure 11:
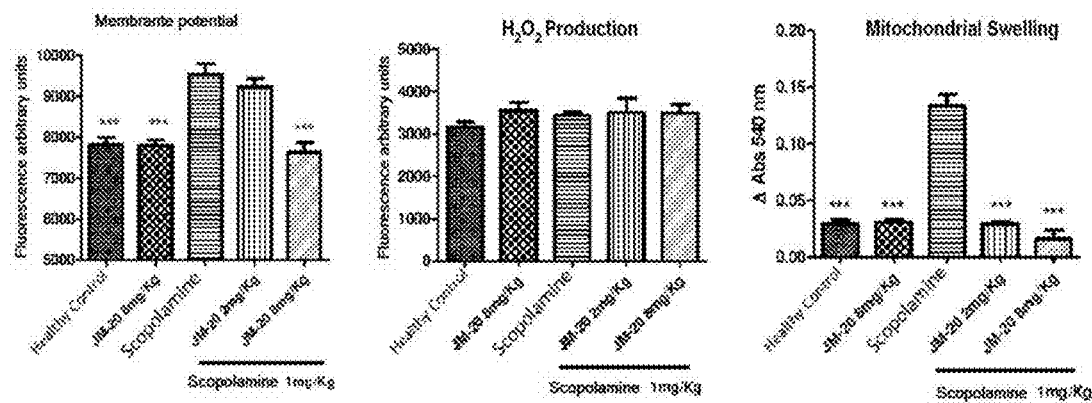
FIG. 11: Effect of JM-20 on mitochondrial dysfunction of cerebral tissue in rats treated with scopolamine. after completing long-term memory studies. Effect of JM-20 on mitochondrial dysfunction of brain tissue in scopolamine-treated rats. The different doses of JM-20 were administered orally 1 h before administration of scopolamine. Brain mitochondria were isolated 24 h after administration of scopolamine and the membrane potential (A), $H_2O_2$ generation (B) and mitochondrial swelling (C) were evaluated. Bars represent the mean±SEM (n=10). *, $p<0.001$; , $p<0.01$ y *, $p<0.05$ relative to the vehicle/scopolamine group 1 mg/Kg, by ANOVA and Tukey's post hoc.

FIG. 11 shows the effect of JM-20 on mitochondrial dysfunction of cerebral tissue in rats treated with scopolamine after completion of long-term memory studies. The different doses of JM-20 were administered orally 1 hour prior to the administration of the scopolamine. Brain mitochondria were isolated 24 hours after administration of the scopolamine and we assessed the membrane potential (A), $H_2O_2$ generation (B) and mitochondrial swelling (C). The bars represent the mean±EEM (n=10). *, $p<0.001$; , $p<0.01$ y*, $p<0.05$ in regards to the vehicle/scopolamine group 1 mg/Kg, by ANOVA and post hoc Tukey.

Figure 12:
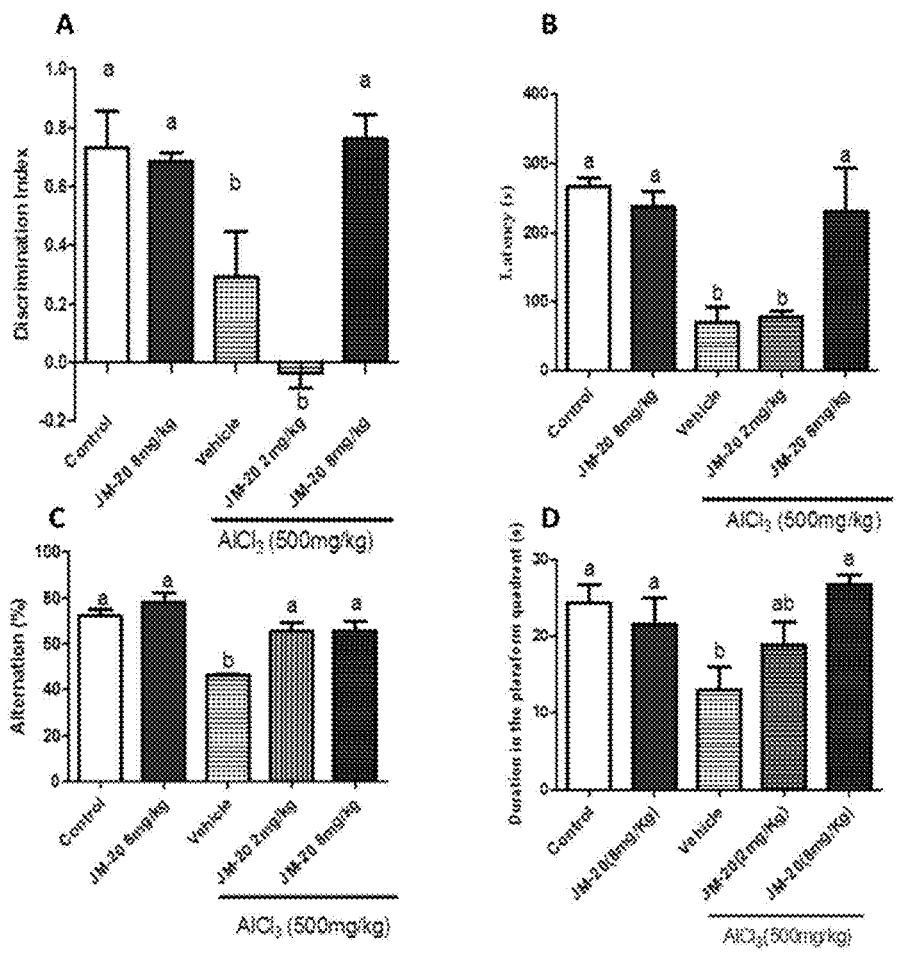
FIG. 12: Effect of JM-20 on the loss of different types of memory induced by aluminum. A) New object recognition test, novelty recognition memory; B) Passive avoidance test, emotional-associative memory; C) Y-maze test, working spatial memory; D) Morris water maze, reference spatial memory. Bars represent the mean±SEM. Different letters show differences between groups: p<0.05; by ANOVA and Tukey's post hoc. *, p<0.001; , p<0.01 y *, p<0.05 relative to the aluminum-treated group 500 mg/Kg, by ANOVA and Turkey's post hoc.
Figure 13:
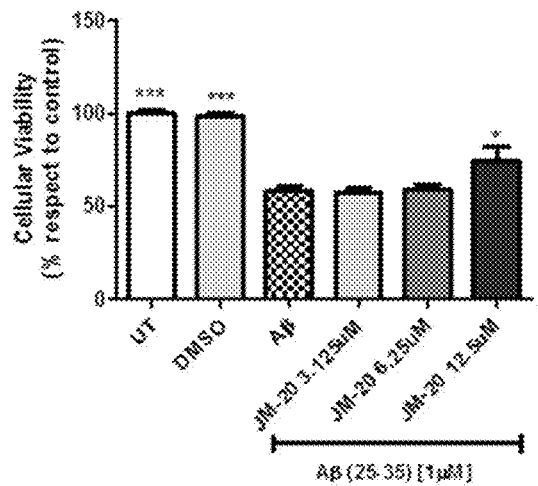
FIG. 13: Effects of JM-20 on damage to cellular viability produced by beta amyloid 25-35 peptide oligomers.

FIG. 12 shows the effect of JM-20 on the loss of different types of memory induced by aluminum. A) Recognition of novel objects test, novel object recognition memory; B) Passive avoidance test, emotional-associative memory; C) Y-maze test, spatial working memory; D) Morris Water Maze spatial reference memory. The bars represent the mean±EEM. Different letters show differences between groups: $p<0.05$, by ANOVA and post hoc Tukey. *, $p<0.001$; , $p<0.01$ y*, $p<0.05$ comparison in regards to the group treated with aluminum 500 mg/Kg, by ANOVA and post hoc Tukey group.

Figure 14:
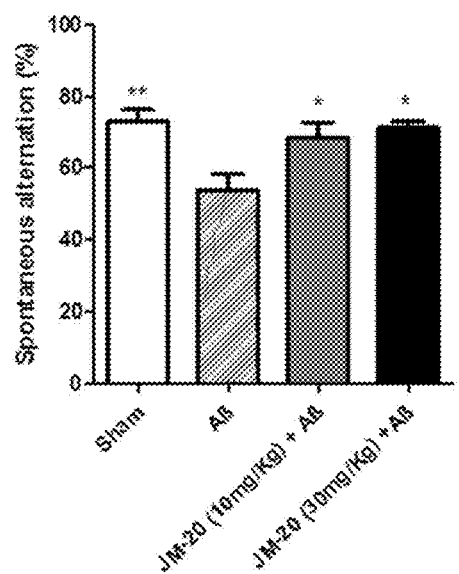
FIG. 14. JM-20 reverts memory loss induced by beta amyloid 25-35 peptide oligomers. JM-20 was administered 7 days after the beta amyloid administration. Bars represent mean±SEM, a comparison is made with respect to the group treated with beta amyloid *, p<0.001; , p<0.01 and *, p<0.05 by ANOVA and Tukey's post hoc.

FIG. 14 shows how JM-20 reverts memory loss induced by beta amyloid 25-35 peptide oligomers. JM-20 was administered 7 days following administration of the beta amyloid. The bars represent the mean±EEM; the comparison is done on the group treated with beta amyloid *, $p<0.001$; , $p<0.01$ y *, $p<0.05$ by ANOVA and post hoc Tukey group.

Vascular Dementia

As a model of vascular dementia, animals (Swiss male albino mice) were submitted to transitory occlusion of the common carotid arteries for 20 minutes and cognitive deterioration was assessed by the Morris Water Maze test.

Figure 15:
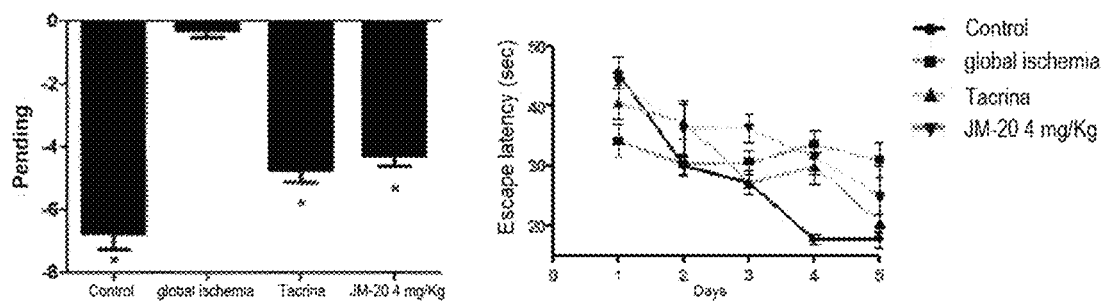
FIG. 15: Effects of JM-20 on cognitive deterioration induced by the transitory occlusion of the common carotid arteries of rats. Animals were administered orally at a dose of 4 mg/Kg, 1 after reperfusion. Data is expressed as mean±SD (n=8, per group). For statistical analysis, a multiple comparison ANOVA and Tukey test were performed. * p<0.01, represents significant differences with respect to untreated ischemic animals.

Results are shown in FIG. 15.

FIG. 15 shows effects of JM-20 on cognitive deterioration induced by the transitory occlusion of the common carotid arteries of rats. The animals were administered oral doses of 4 mg/Kg, 1 after reperfusion. Data is expressed as the mean±DE (n=8, per group). For statistical analysis we carried out ANOVA and Tukey multiple comparison tests, * $p<0.01$, represents significant differences in regards to ischemic animals without n treatment.

Unilateral Lesions of the Sustantia *nigra pars* compacta by 6-Hydroxydopamine Injection Materials and Methods Experiment Animals Male adult Wistar rats were used, weighing between 200 and 250 grams at the start of the experiment, coming from the National Laboratory Animal Production Center (CENPALAB), Havana, Cuba. The animals were kept at the Center for the Research and Development of Medicines (CIDEM) in plastic translucent boxes at an average temperature of 23° C. (22±2° C.), with food and water supplies ad libitum and 12-hour periods of light and dark.

Ethical Considerations

In this study the norms established in the ethics code for experiments using animals was respected.

We guaranteed the animals' genetic authenticity by acquiring the animals at recognized breeding centers. This procedure avoids using genetically contaminated animals. From a biological point of view the importance of genetic quality for research lies in the fact that experiment results may be reproduced in any other location where they may be repeated and from the ethical point of view it ensures the least number of animals need to be used.

During the research, animals were kept in the best accommodation conditions possible. They were kept at temperatures of 23° C., thereby being within the commitment range set for tropical areas (22±2 C). Temperature control is important if we keep in mind that high temperatures cause stress for the animals and temperatures of over 38° C. may cause their death. The periods of light and dark to which they were exposed lasted 12 hours since photoperiodicity directly and/or indirectly controls the circadian, biochemical and hormonal rhythms.

Administration of the Compound

JM-20 was administered in 3 different doses: 10, 20 and 40 mg/Kg, 24 hours after inducing damage and on a daily basis for 7 days. The compound was prepared in carboxymethylcellulose (CMC) at 0.05%, intragastrically with a cannula. There were 5 experimentation groups: Group I (vehicle/saline with ascorbic acid, n=6), Group II (animals affected with 6-OHDA, n=8), Group III (animals affected with 6-OHDA and co-treated with 10 mg/Kg JM-20, n=8), Group IV (animals affected with 6-OHDA and co-treated with 20 mg/Kg JM-20, n=8) and Group V (animals affected with 6-OHDA and co-treated with 40 mg/Kg JM-20 n=8). All behavioral studies were run at 7 days.

Data Processing

Statistical analyses were done with the GraphPadPrism Version. 5.01.2007 package. Results indicate the mean±SEM of the percentage of vitality as compared to the untreated control cells. In all cases, variance analysis was done (OneWay ANOVA) followed up by the Dunet Test (GraphPadPrism 5) to determine significant differences with a signification level of $p<0.05$ (*), $p<0.01$ () y $p<0.001$ (*) in regards to a control used in the experiment. In order to compare all values obtained in the experiment to various controls and against each other, we ran the Tukey Test (GraphPadPrism 5), with a signification level of $p<0.05$ (*), $p<0.01$ () y $p<0.001$ (*).

Lesion Methods in Experiment Models Designed for Rats

Unilateral Lesions of the Sustantia *Nigra pars compacta* by 6-Hydroxydopamine Injection in Rats For the purpose of proceeding to unilateral dopaminergic denervation of the striate body (right hemisphere) the rats were anesthetized with Chloral Hydrate [0.4 g/kg weight, i.p., Merck (Darmstadt, Germany)] and placed into a frame designed for stereotactic surgery (Stoelting Instruments, USA.), where they were injected in the right substantia *nigra pars compacta* with saline solution neurotoxin 6-OHDA-HBr (8 µg/3 µL, also containing 0.2 mg/ml of ascorbic acid as an antioxidant) (Pavón Fuentes, Nancy (2007) Efecto de la inactivación de los receptores dopaminérgicos D2 y de la manipulación del núcleo subtalámico sobre la conducta motora en modelos de hemiparkinsonismo en roedores. Doctor en Ciencias de una Especialidad, Universidad de Ciencias Médicas de La Habana). Coordinates were calculated taking Bregma as a point of reference in accordance with the Paxinos and Watson Atlas [Paxinos, G. and Watson, C., The rat brain in stereotaxic coordenates. 2nd the Academic Press. New York, 1986], referred to in Table 1.

TABLE 1

Stereotaxic coordinates expressed in mm in regards to Bregma (except the DV referring to the dural surface)

| | Coordinates |
|---|---|
| AP | −4.4 mm |
| ML | 1.2 mm |
| DV | 7.8 mm |
| Incisive bar | −2.4 mm under the interaural line |

Once in place, the neurotoxin was slowly injected at a flow speed of 1 µl/min, with a Manilton syringe (3 µl), remaining in situ for 5 min. after the injection had finished.

IV. Behavioral Tests

A. Cylinder Test

In this test rats were placed inside a transparent acrylic cylinder 20 cm in diameter and 30 cm high which did not allow the animal to reach the edge. The cylindrical shape favors the innate behavior of vertical exploration of the wall with their back extremities when rats were placed into a site that they did not know. (Chan, H., Paur, H., Vernon, A. C., Zabarsky, V., Datla, K. P., Croucher, M. J., Dexter, D. T., 2010. Neuroprotection and functional recovery associated with decreased microglial activation following selective activation of mGluR2/3 receptors in a rodent model of Parkinson's disease. ParkinsonsDis.pii, 190450). After placement of the animal, the number of touches made by the animal with both front paws, the right or the left, is quantified up to a total of 20 touches per animal on the recipient's wall.

Animals unilaterally affected with 6-OHDA tend to use the paw which is counter-lateral to the affectation to a lesser extent, in our case the left paw. The percentage of asymmetry presented by each animal is quantified by the following formula (Roof R L, Schielke G P, Ren X, Hall E D (2001) A comparison of long-term functional outcome after 2 middle cerebral artery occlusion models in rats. Stroke 32: 2648-2657).

(% ipsilateral touches)−(% contralateral touches)=(% Asymmetry)

Exploratory Activity

In order to assess the vertical exploratory activity of animals we used the Exploratory Activity Test; the animal is placed in a clear Plexiglas cubicle, 41×41×33 (h) cm, (UGO BASILE, MultipleActivityCage Cat. No. 47420. Data output is managed by 52050-04 Data Acquisition Software Package (Windows® based). The cubicle is supported on a robust base made of black Plexiglas that has 4 vertical steel bars with steel grooves so that the horizontal/vertical detection systems are correctly affixed. The sensors are IR light emission systems capable of registering animal movements by shapes, or rather vertical exploration. Data is monitored on a computer. Animals are placed in the center of the box so that they can explore it. The box is placed in a room isolated from the researcher and environmental noise and having low lighting, for a period of 5 minutes. The researcher takes the number of times the animal vertically explores the box's walls, when the sensor's light beams in the box are interrupted (Cools, A. R., R. Brachten, D. Heeren, A. Willemen, and B. Ellenbroek, 1990. Search after neurobiological profile of individual-specific features of Wistar rats. Brain Res. Bull. 24: 49-69). Results are presented in FIG. 16.

Figure 16:
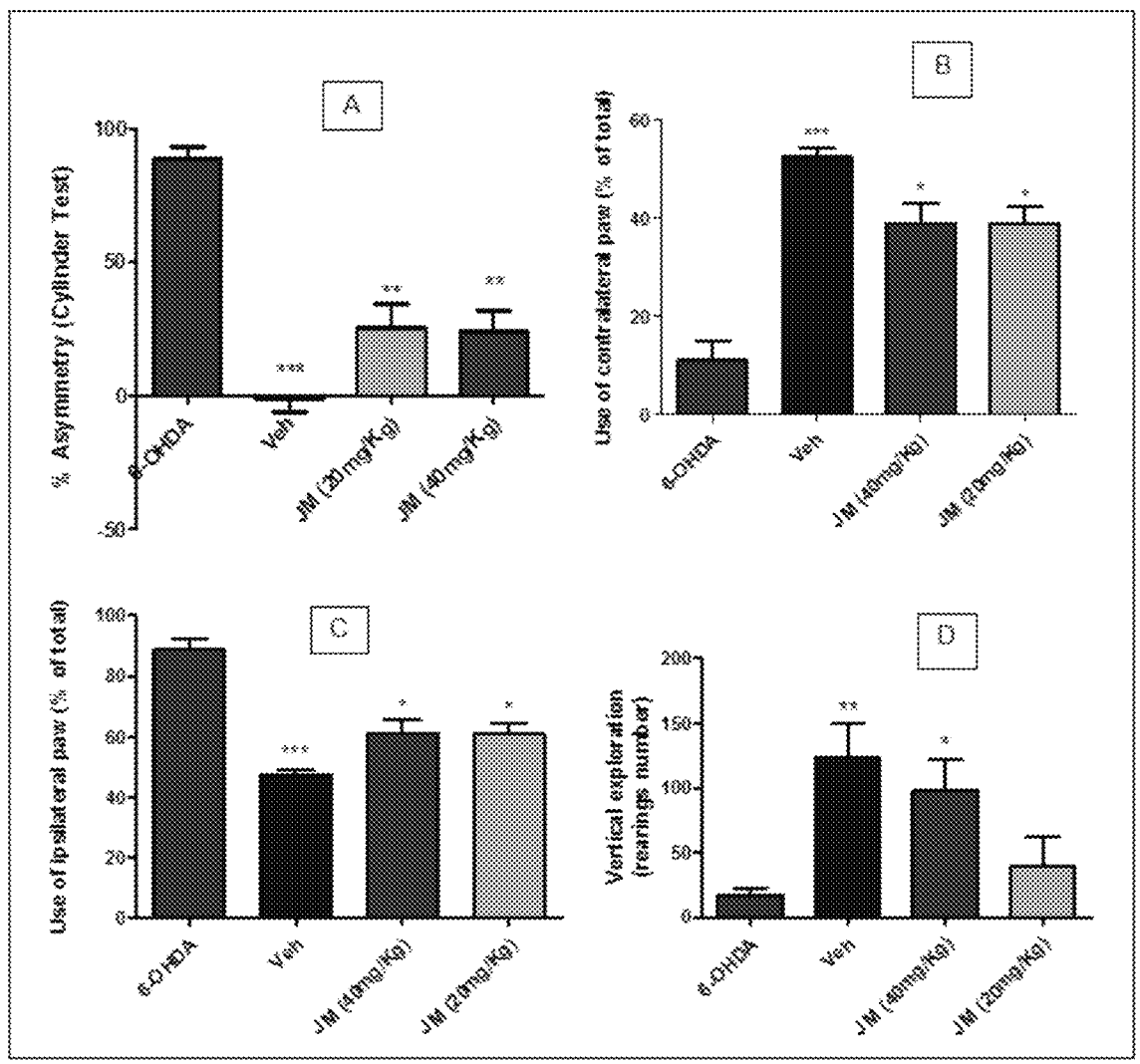
FIG. 16: Neuroprotector effect of JM-20 on damage induced by 6-OHDA in male Wistar rats after 7 days of treatment. (A) % reduction in asymmetry (cylinder test), animals treated with JM-20 showed a decrease in motor damage with respect to injured animals without treatment. (B) increased use of contralateral leg when there is injury and (C) normal values of the use of the ipsilateral leg (50%) in injured animals and rerated with both doses of JM-20 (40 and 20 mg/Kg). (D) Animals treated with JM-20 increased vertical exploration, which was statistically different from the 40 mg/Kg dose with respect to untreated injured animals.

FIG. 16 shows the neuroprotector effect of JM-20 on damage induced by 6-OHDA in male Wistar rats after 7 days of treatment. (A) reduction of the % of asymmetry (cylinder test), animals treated with JM-20 showed diminished motor damage in comparison with damaged animals without treatment. (B) increased use of the paw contralateral to the damage and (C) normal values of the use of the ipsilateral paw (50%~), in damaged animals and those treated with both doses of JM-20 (40 and 20 mg/Kg). (D) Animals treated with JM-20 increased their vertical exploration, being statistically different to the dose of 40 mg/Kg in regards to untreated damaged animals.

Tonic Pain

We studied the effect of JM-20 (10, 20, 40 mg/Kg, p.o) on behaviors related to pain in a tonic pain model (5% formalin test) in rats. (Dubuisson D, Dennis S G. The formalin test: a quantitative study of the analgesic effects of morphine, meperidine and brain-stem stimulation in rats and cats. Pain 1977; 4:161-174).

Results are presented in FIGS. 17 A, 17 B and 18.

Figure 17A:
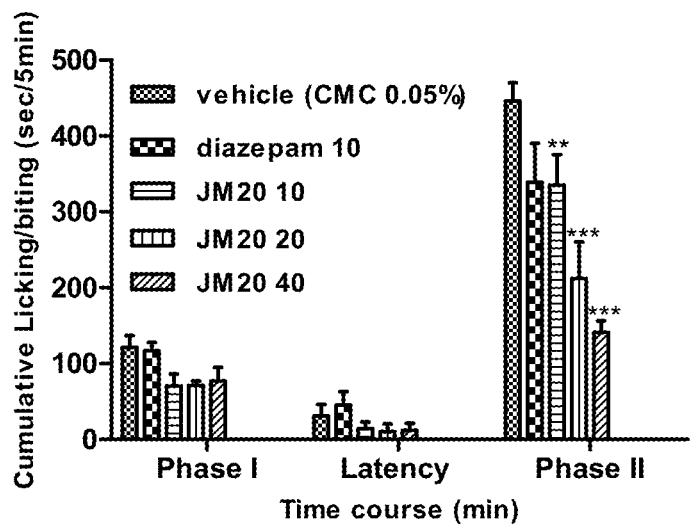
FIG. 17A: Effects of JM-20 on licking/biting behavior after injecting 5% formalin on the plantar surface of the rat's paw. Effect of JM-20 (10-40 mg/Kg, 10 mL/Kg, p.o.), diazepam 10 mg/Kg or vehicle (CMC, 0.05%) on licking/biting behavior after injection of 5% formalin into the plantar surface of the rat's paw. The data is presented as a cumulative mean of the licking/biting time±SEM during phase I (0-5 min), latency (5-15 min) and phase II (15-45 min) of the formalin test, n=7 per group, ***p<0.001 represent significant differences with respect to the vehicle-treated control group (one way ANOVA followed by Dunnett's a posteriori).

FIG. 17A shows effects of JM-20 (10-40 mg/Kg, 10 mL/Kg, p.o.), diazepam 10 mg/Kg or vehicle (CMC, 0.05%) on licking/biting behavior after injecting 5% formalin on the plantar surface of the rat's paw. The data is presented as accumulative mean of the time of licking/biting±EEM during Phase I (0-5 min), Latency (5-15 min) and Phase II (15-45 min) or the formalin test, n=7 per group, ***p<0.001 represents significant differences in regards to the control group treated with the vehicle (ANOVA for one route followed by Dunnett's a posteriori).

Figure 17B:
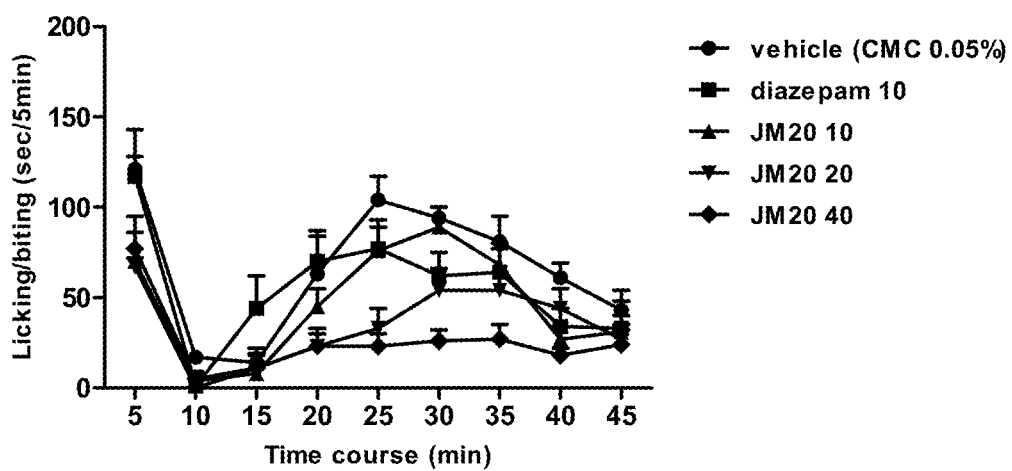
FIG. 17B. Time course of the effect of JM-20 on licking/biting behavior after injection of 5% formalin on the plantar surface of the rat's paw. Time course of the effect of JM-20 (10-40 mg/Kg, 10 mL/Kg, p.o.), diazepam 10 mg/Kg or vehicle (CMC, 0.05%) on licking/biting behavior after injection of 5% formalin into the plantar surface of the rat's paw. The data is presented as a mean of the licking time/biting time (/5 min/sec)±SEM during the 45 minutes of the test, n=7 per group.

FIG. 17B shows the time course of the effect of JM-20 (10-40 mg/Kg, 10 mL/Kg, p.o.), diazepam 10 mg/Kg or vehicle (CMC, 0.05%) on licking/biting behavior after injection of 5% formalin on the plantar surface of the rat's paw. Data is presented as the mean of licking/biting time (/5 min/sec)±EEM during the 45 minutes of the test, n=7 per group.

Figure 18:
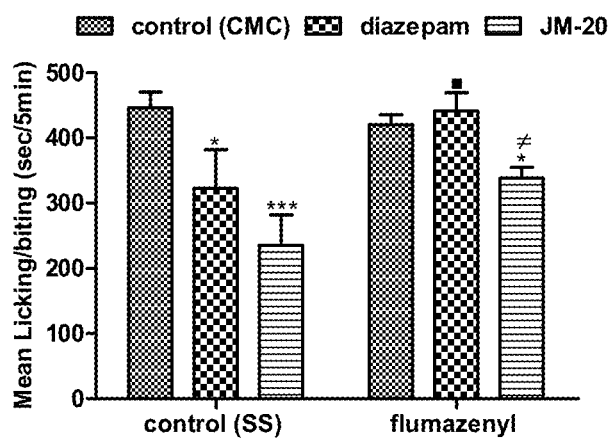
FIG. 18: Influence of pre-treatment with flumazenyl on the antihypernociceptive effect of JM-20 on Phase II of the 5% formalin test. Influence of pre-treatment of animals with flumazenil (10 mg/kg, i.p.) on the antihypernociceptive effect of JM-20 on phase II of 5% formalin test. Each column represents the reactivity time of 6-10 animals per group as mean±SEM, * P<0.05, *P<0.001 represent statistical differences between treated and control groups (vehicle only), *P<0.05 represents statistical difference between groups treated with diazepam in the presence or absence of flumazenil, ≠P<0.05 represents statistical differences between groups treated with JM-20 in the presence or absence of flumazenil.

FIG. 18 shows the influence of pre-treating animals with flumazenyl (10 mg/Kg, i.p) on the antihypernociceptive effect of JM-20 on Phase II of the 5% formalin test. Each column represents the reaction time of 6-10 animals per group as the mean±EEM, * P<0.05, *P<0.001 represents the statistical differences between treated and control groups (only vehicle), **P<0.05 represents statistical differences between groups treated with diazepam in the presence or absence of flumazenil, 1p<0.05 represents statistical differences between groups treated with JM-20 in the presence or absence of flumazenyl.

Neuropathic Pain

We studied the effect of JM-20 on the chronic constriction of the sciatic nerve model (CCI), an NP model (Bennett M I, Rayment C, Hjermstad M, Aass N, Caraceni A, Kaasa S. Prevalence and aetiology of neuropathic pain in cancer patients: A systematic review. Pain 2012; 153:359-365) Results are presented in FIG. 19-23.

Figure 19:
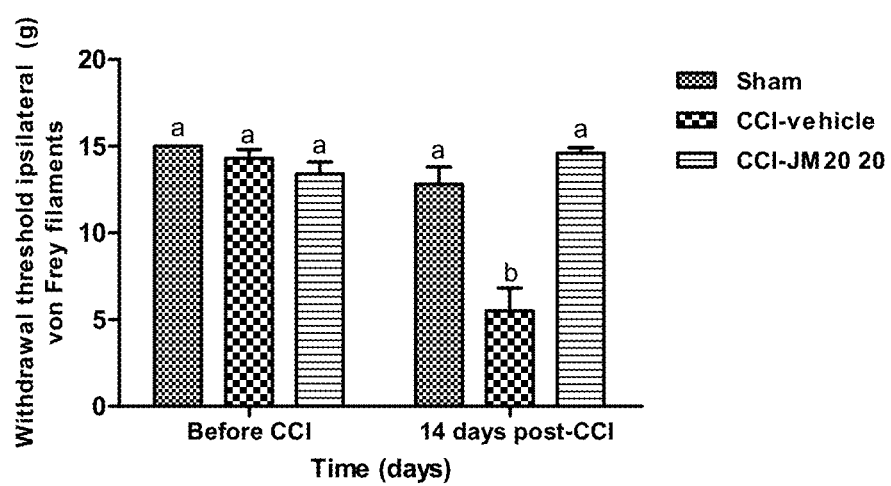
FIG. 19: Effects of JM-20 on mechanical allodynia in the ipsilateral paw of the CCI rats 14 days after surgery. Effect of JM-20 (20 mg/Kg, 10 mL/Kg, p.o.) or vehicle (CMC, 0.05%) on mechanical allodynia in the ipsilateral paw in CCI rats 14 days after surgery, determined by measuring the paw withdrawal response to the stimulation of von Frey filaments. Data are presented as media±SEMI of 50% response threshold, n=7 per group. Different letters represent significant differences between the groups (one way ANOVA followed by Bonferronni's a posteriori).

FIG. 19 shows the effects of JM-20 (20 mg/Kg, 10 mL/Kg, p.o.) or the vehicle (CMC, 0.05%) on mechanical allodynia in the ipsilateral paw of the CCI rats 14 days after surgery, determined by measuring the paw withdrawal response with von Frey filament stimulation. Data is presented as the mean±EEM of the 50% of the response threshold, n=7 per group. Different letters represent significant differences between the groups (ANOVA for one route followed by Bonferronni's a posteriori).

Figure 20:
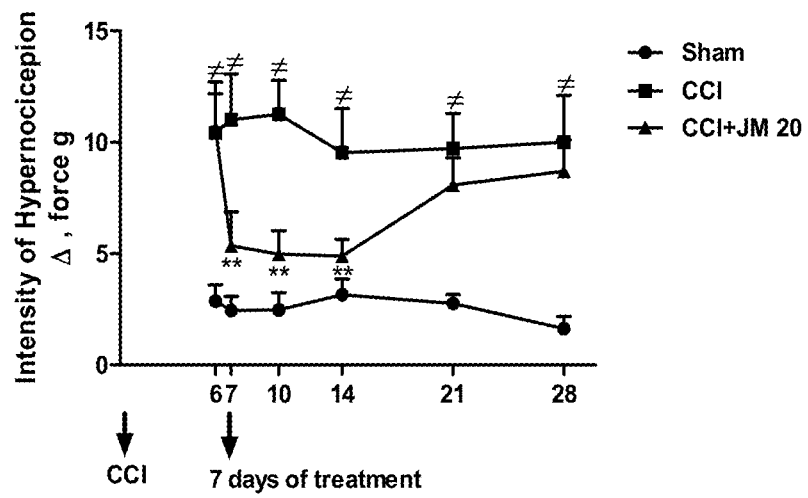
FIG. 20: Effects of JM-20 on the intensity of mechanical hypernociception of the ipsilateral paws of CCI rats determined by measuring the paw withdrawal response when stimulated with electronic von Frey. Effect of JM-20 (20/Kg, 10 mL/Kg, p.o.) or vehicle (CMC, 0.05%) on the intensity of mechanical hypernociception in the ipsilateral paw in CCI rats, determined by measuring the paw withdrawal response to stimulation with an electronic von Frey. Data is presented as mean±SEM of the difference (Δ) of the withdrawal threshold in grams calculated from the subtraction of the mean of the three measurements at different time intervals from the mean of the three measurements at time 0, n=7 per group **p<0.01 represent significant differences with respect to the control group treated with vehicle #p<0.05 represent significant differences with respect to the False CCI group (one way ANOVA followed by Bonferronni's a posteriori).

FIG. 20 shows the effects of JM-20 (20/Kg, 10 mL/Kg, p.o.) or vehicle (CMC, 0.5%) on the intensity of mechanical hypernociception of the ipsilateral paws of CCI rats determined by measuring the paw withdrawal response when stimulated with electronic von Frey. Data is presented as the mean±EEM of the threshold difference (A) for withdrawal in grams calculated on the basis of subtracting the mean of the three measurements of different time intervals from the mean of the three time measurements 0, n=7 per group **p<0.01 represents significant differences in regards to the control group treated with the vehicle, #p<0.05 represents significant differences in regards to the Sham CCI Group (ANOVA for one route followed by Bonferronni's a posteriori).

Figure 21:
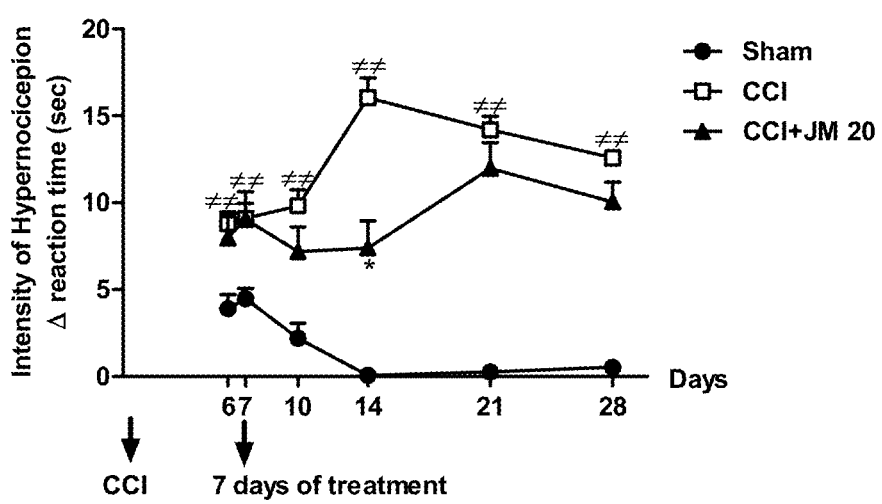
FIG. 21. Effects of JM-20 (20 mg/Kg, 10 mL/Kg, p.o.) or vehicle (CMC, 0.05%) on mechanical hypernociception to constant pressure on the paws by a modification to the classic Randal Selito or SH Ferreira Test. Data is presented as mean±SEM of the difference (Δ) of the reaction time calculated by the subtraction of the measurement at the different time intervals from the measurement at time 0, n=7 per group *p<0.05 represent significant differences with respect to the control group treated with vehicle ##p<0.01 represent significant differences with respect to the False CCI group (one way ANOVA followed by Bonferronni's a posteriori).

FIG. 21 shows the effects of JM-20 (20 mg/Kg, 10 mL/Kg, p.o.) or vehicle (CMC, 0.05%) on mechanical hypernociception to constant pressure on the paws by a modification to the classic Randal Selito or SH Ferreira Test. Data is presented as the mean±EEM of the difference (Δ) of the reaction time calculated by subtracting the measurement of the different time intervals from the time measurement 0, n=7 per group *p<0.05 represents significant differences in regards to the control group treated with the vehicle, ##p<0.01 represents significant differences in regards to the Sham CCI Group (ANOVA for one route followed by Bonferronni's a posteriori).

Figure 22:
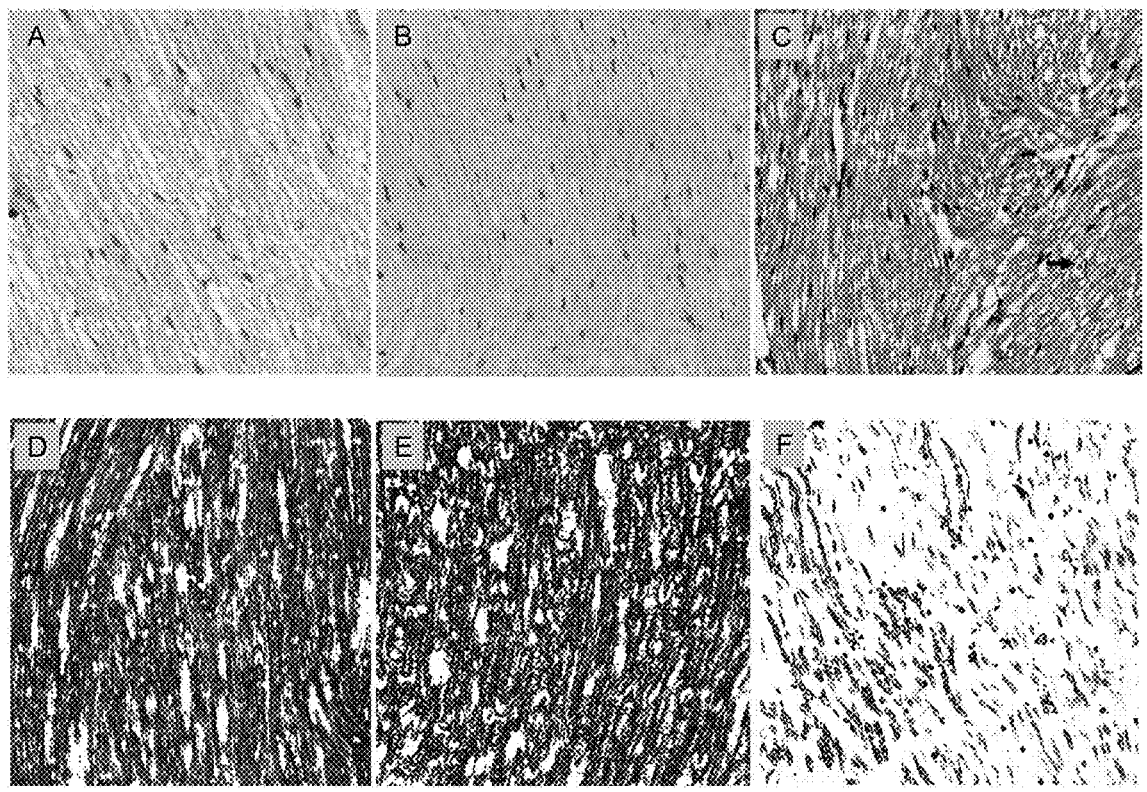
FIG. 22: Effects of treatment with JM-20 at repeated doses for 7 days starting on Day 7 Post-CCI on histological changes induced by CCI (Wallerian degeneration) at 14 days after surgery. A, B and C show the longitudinal section of the sciatic nerve 5 mm distal to the lesion of false CCI, CCI treated with JM-20 and vehicle-treated rats, respectively (H/E coloring). It is observed the increase of cellularity in the CCI animals relative to the false animals operated as a result of the proliferation of Schawann cells and the infiltration of macrophages and the loss of ordered alignment of axons associated to their myelin sheaths with respect to the false-CCI. The arrow indicates one of the many Schwann cell digestion chambers containing a myelin ovoid (oval red mass). D, E, F show sections of the same animals but colored by the luxol fast blue (LFB) technique specific for myelin staining. B and E. Reduction in CCI-induced nerve fiber disruption and cell count increase and myelin sheath degradation in JM-20 treated animals, particularly this latter effect is needed in E.

FIG. 22 shows the effects of treatment with JM-20 (20 mg/Kg, p.o) at repeated doses for 7 days starting on Day 7 Post-CCI on histological changes induced by CCI (Wallerian degeneration) at 14 days after surgery. A, B and C show the longitudinal section of the sciatic nerve 5 mm distal to the lesion on CCI Sham rats, CCI treated with JM-20 and treated with vehicle respectively (H/E coloration). We can observe the increase in cellularity in CCI animals relatively compared with sham operated animals as the result of the proliferation of Schawann cells and the infiltration of macrophages and the loss of an orderly alignment of axons associated to their myelin sheathes as compared to the sham-CCI. The arrow indicates one of the many digestion chambers of Schawann cells containing a myelin ovoid (reddish oval mass). D, E, F show sections from the same animals but they are colored by the luxol fast blue (LFB) technique, a specific technique for myelin tincture. B and E: reduced disorganization of the nerve fibers induced by CCI and increased number of cells and the degradation of myelin sheathes in animals treated with JM-20, particularly this last effect specified in E.

Figure 23:
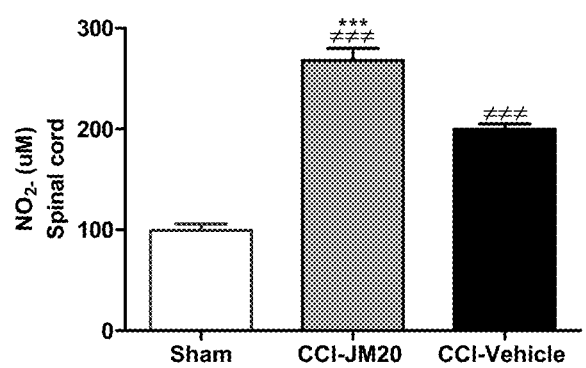
FIG. 23: Effects of JM-20 on spinal concentrations of nitrates as an indicator of nitric oxide concentrations. Effect of JM-20 (20 mg/Kg, 10 mL/Kg, p.o.) or vehicle (CMC, 0.05%) on spinal nitrite concentrations as an indicator of nitric oxide concentration. Data is presented as mean±SEM, n=7 per group ***p<0.001 represent significant differences with respect to the control group treated with vehicle ###p<0.001 represent significant differences with respect to the False CCI group (one way ANOVA followed by Bonferronni's a posteriori).

FIG. 23 shows the Effects of JM-20 (20 mg/Kg, 10 mL/Kg, p.o.) or vehicle (CMC, 0.05%) on spinal concentrations of nitrates as an indicator of nitric oxide concentrations. Data I presented as the mean±EEM, n=7 per group, ***p<0.001 represents significant differences regarding the control group treated with the vehicle, ###p<0.001 represents significant differences regarding the Sham CCI Group (ANOVA for one route followed by Bonferronni's a posteriori).

Carragenin-Induced Peritonitis

Subsequently we designed different experiments in the CA induced peritonitis model in rodents in order to explore the possible anti-inflammatory activity of JM-20 in these conditions.

Figure 24:
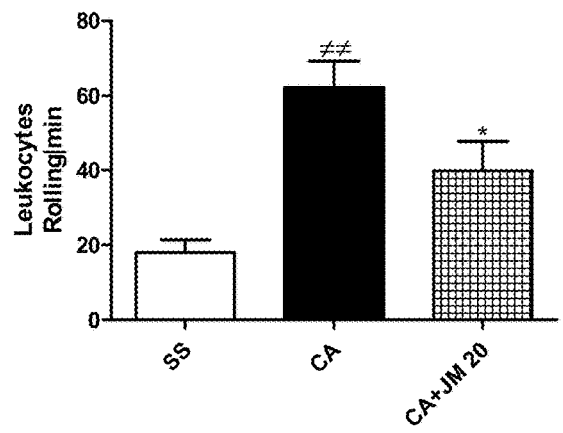
FIG. 24 A & B: Effects of JM-20 on peritoneal inflammatory response induced by carragenin (500 µg/cavity) in rats. A. Leukocyte rolling and B their adhesion to the vascular endothelium in the mesentery. Effect of JM-20 (20 mg/Kg, 10 mL/Kg, p.o.) or vehicle (CMC, 0.05%) on peritoneal inflammatory response induced by carragenin (500 pg/cavity) in mice. A. The enrollment of the leukocytes and their adhesion to the vascular endothelium in the mesentery were determined by intravital microscopy 4 h after induction of inflammation. Data is presented as mean±SEM, n=6 per group, *p<0.05, **p<0.01 represent significant differences relative to the control group treated with vehicle, ####p<0.001, ##p<0.01 represent significant differences relative to control with intraperitoneal saline (one way ANOVA followed by Newman-Keuls or Bonferronni's a posteriori in each respective case).
Figure 24:
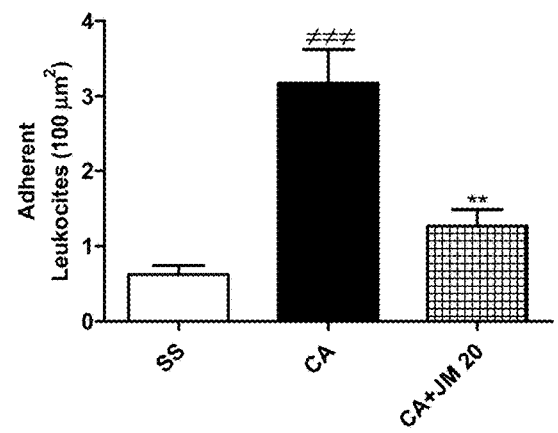
Figure 24:
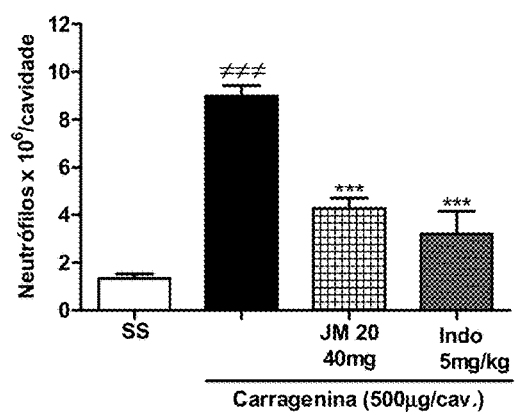
Figure 24:
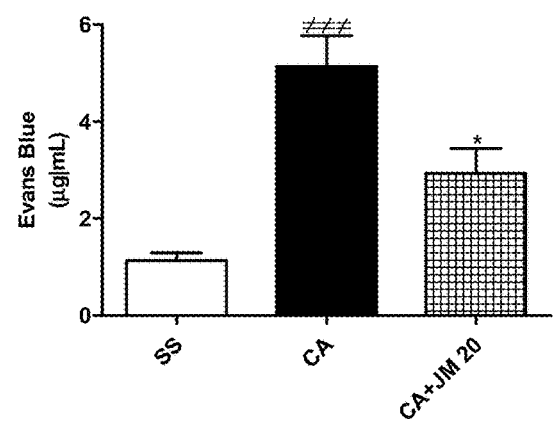
Figure 24:
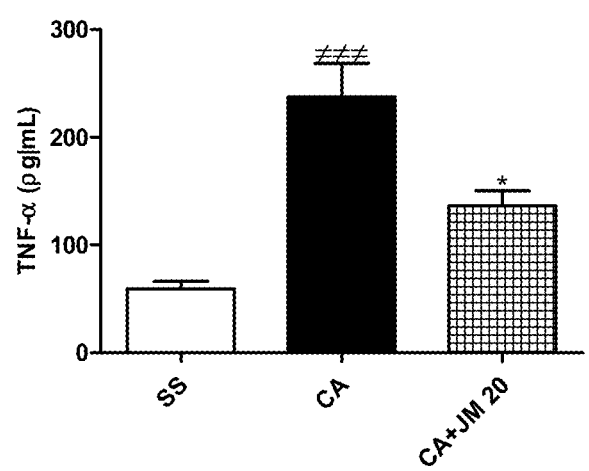

Results are shown in FIGS. 24 A-E.

FIG. 24 shows the effects of JM-20 (20 mg/Kg, 10 mL/Kg, p.o.) or vehicle (CMC, 0.05%) on peritoneal inflammatory response induced by carragenin (500 µg/cavity) in rats. A. Leukocyte rolling and B their adhesion to the vascular endothelium in the mesentery were determined by intravital microscope 4 hours after induction of the inflammation. C. Migration of leukocytes towards the peritoneal cavity and D. vascular permeability (µg/mL) were determined 4 hours post-CA. E Effects on concentrations of the tumor necrosis factor (TNFα) in the peritoneal fluid 4 hours after the carragenin injection. Data is presented as the mean±EEM, n=6 per group, *p<0.05, **p<0.01 represents significant differences in regards t the control group treated with the vehicle, ###p<0.001, ##p<0.01 represents significant differences in regards to the control with intraperitoneal saline solution (ANOVA for one route followed by Newman-Keuls or Bonferronni's a posteriori in each respective case).

The invention claimed is:

1. A method for the treatment of Alzheimer's disease, the method comprising administering to a subject in need thereof a pharmaceutical composition comprising a therapeutically effective amount of a compound of formula III or a pharmaceutically acceptable salt thereof

III

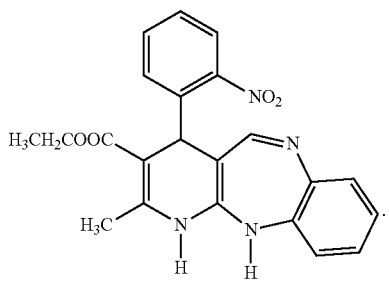

and a pharmaceutically acceptable carrier.

2. The method of claim 1, wherein the pharmaceutically acceptable salt thereof is a hydrochloric acid salt, hydrobromic acid salt, fumaric acid salt, phosphoric acid salt, or a sulfuric acid salt.

3. The method of claim 1, wherein the pharmaceutical composition is a tablet, a capsule, a solution, a microgranule, a nanoparticle, a pellet, or a powder.

4. A method for the treatment of neuropathic pain, the method comprising administering to a subject in need thereof a pharmaceutical composition comprising a therapeutically effective amount of a compound of formula III or a pharmaceutically acceptable salt thereof

III

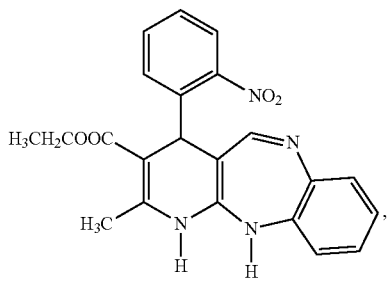

and a pharmaceutically acceptable carrier.

5. The method of claim 4, wherein the pharmaceutically acceptable salt thereof is a hydrochloric acid salt, hydrobromic acid salt, fumaric acid salt, phosphoric acid salt, or a sulfuric acid salt.

6. The method of claim 4, wherein the pharmaceutical composition is a tablet, a capsule, a solution, a microgranule, a nanoparticle, a pellet, or a powder.

7. A method for the treatment of vascular dementia, the method comprising administering to a subject in need thereof a pharmaceutical composition comprising a therapeutically effective amount of a compound of formula III or a pharmaceutically acceptable salt thereof

III

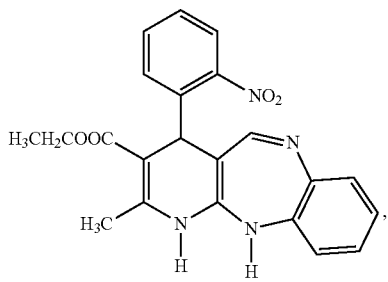

and a pharmaceutically acceptable carrier.

8. The method of claim 7, wherein the pharmaceutically acceptable salt thereof is a hydrochloric acid salt, hydrobromic acid salt, fumaric acid salt, phosphoric acid salt, or a sulfuric acid salt.

9. The method of claim 7, wherein the pharmaceutical composition is a tablet, a capsule, a solution, a microgranule, a nanoparticle, a pellet, or a powder.

10. A method for the treatment of Parkinson's disease, the method comprising administering to a subject in need thereof a pharmaceutical composition comprising a therapeutically effective amount of a compound of formula III or a pharmaceutically acceptable salt thereof

III

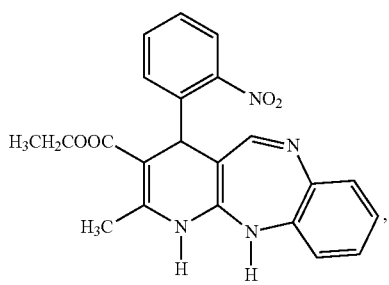

and a pharmaceutically acceptable carrier.

11. The method of claim 10, wherein the pharmaceutically acceptable salt thereof is a hydrochloric acid salt, hydrobromic acid salt, fumaric acid salt, phosphoric acid salt, or a sulfuric acid salt.

12. The method of claim 10, wherein the pharmaceutical composition is a tablet, a capsule, a solution, a microgranule, a nanoparticle, a pellet, or a powder.

13. A method for the treatment of memory loss, the method comprising administering to a subject in need thereof a pharmaceutical composition comprising a therapeutically effective amount of a compound of formula III or a pharmaceutically acceptable salt thereof

III

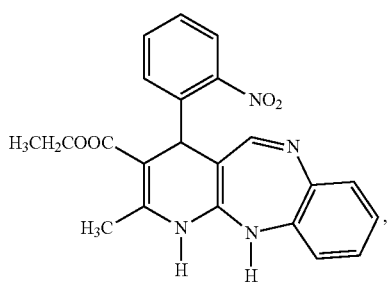

and a pharmaceutically acceptable carrier.

14. The method of claim 13, wherein the pharmaceutically acceptable salt thereof is a hydrochloric acid salt, hydrobromic acid salt, fumaric acid salt, phosphoric acid salt, or a sulfuric acid salt.

15. The method of claim 13, wherein the pharmaceutical composition is a tablet, a capsule, a solution, a microgranule, a nanoparticle, a pellet, or a powder.

16. The method of claim 13, wherein the memory loss is associated with dementia.

17. The method of claim 16, wherein the dementia is Alzheimer's disease or vascular dementia.

* * * * *

UNITED STATES PATENT AND TRADEMARK OFFICE
CERTIFICATE OF CORRECTION

| | |
|---|---|
| PATENT NO. | : 11,098,039 B2 |
| APPLICATION NO. | : 16/099116 |
| DATED | : August 24, 2021 |
| INVENTOR(S) | : Yanier Núñez Figueredo et al. |

Page 1 of 1

It is certified that error appears in the above-identified patent and that said Letters Patent is hereby corrected as shown below:

In the Specification

Column 6, Line 61:  now reads "Griffin µW"
should read --Griffin JW--

Column 10, Line 10:  now reads "usefulness f JM-20"
should read --usefulness of JM-20--

Column 12, Line 49:  now reads "of Schawann cells"
should read --of Schwann cells--

Column 17, Line 37:  now reads "being a better salient group that chloride"
should read --being a better salient group than chloride--

Column 29, Line 47:  now reads "of the threshold difference (A)"
should read --of the threshold difference (Δ)--

Column 30, Line 55:  now reads "in regards t the"
should read --in regards to the--

Signed and Sealed this
Twenty-fifth Day of October, 2022

Katherine Kelly Vidal
*Director of the United States Patent and Trademark Office*